(12) United States Patent
Vappou et al.

(10) Patent No.: US 9,585,631 B2
(45) Date of Patent: Mar. 7, 2017

(54) DEVICES, METHODS, AND SYSTEMS FOR MEASURING ELASTIC PROPERTIES OF BIOLOGICAL TISSUES USING ACOUSTIC FORCE

(75) Inventors: Jonathan Vappou, New York, NY (US); Elisa Konofagou, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 182 days.

(21) Appl. No.: 13/701,116

(22) PCT Filed: Jun. 1, 2011

(86) PCT No.: PCT/US2011/038798
§ 371 (c)(1),
(2), (4) Date: May 30, 2013

(87) PCT Pub. No.: WO2011/153268
PCT Pub. Date: Dec. 8, 2011

(65) Prior Publication Data
US 2013/0237820 A1    Sep. 12, 2013

Related U.S. Application Data

(60) Provisional application No. 61/427,169, filed on Dec. 24, 2010, provisional application No. 61/350,369, filed on Jun. 1, 2010.

(51) Int. Cl.
*A61B 8/00* (2006.01)
*A61B 8/08* (2006.01)
*G06T 7/00* (2006.01)
*G01S 7/52* (2006.01)

(52) U.S. Cl.
CPC ............ *A61B 8/0858* (2013.01); *A61B 8/485* (2013.01); *G01S 7/52042* (2013.01); *G06T 7/0012* (2013.01)

(58) Field of Classification Search
None
See application file for complete search history.

(56) References Cited

U.S. PATENT DOCUMENTS

| | | |
|---|---|---|
| 3,598,111 A | 8/1971 | Kahn et al. |
| 4,777,599 A | 10/1988 | Dorogi et al. |
| 5,107,837 A | 4/1992 | Ophir et al. |

(Continued)

FOREIGN PATENT DOCUMENTS

| | | |
|---|---|---|
| WO | WO 2010044385 | 4/2010 |
| WO | WO 2010063951 | 6/2010 |

OTHER PUBLICATIONS

Vappou et al., "Quantitative Viscoelastic Parameters Measured by Harmonic Motion Imaging." Phys. Med. Biol. vol. 54. Published May 19, 2009. pp. 3579-3594.*

(Continued)

*Primary Examiner* — James Kish
(74) *Attorney, Agent, or Firm* — Potomac Law Group, PLLC; Mark Catan

(57) ABSTRACT

A device, method, and system for using an acoustic radiation force resulting from focused ultrasound energy in order to generate an internal force remotely and to measure quantitatively tissue elasticity in vivo and non-invasively.

33 Claims, 10 Drawing Sheets

(56) References Cited

U.S. PATENT DOCUMENTS

| | | | |
|---|---|---|---|
| 5,178,147 | A | 1/1993 | Ophir et al. |
| 5,309,914 | A | 5/1994 | Iinuma |
| 5,435,310 | A | 7/1995 | Sheehan et al. |
| 5,601,084 | A | 2/1997 | Sheehan et al. |
| 5,606,971 | A | 3/1997 | Sarvazyan |
| 5,662,113 | A | 9/1997 | Liu |
| 5,722,411 | A | 3/1998 | Suzuki et al. |
| 5,810,731 | A | 9/1998 | Sarvazyan et al. |
| 5,840,028 | A | 11/1998 | Chubachi et al. |
| 5,928,151 | A | 7/1999 | Hossack et al. |
| 6,102,864 | A | 8/2000 | Hatfield et al. |
| 6,102,865 | A | 8/2000 | Hossack et al. |
| 6,123,669 | A | 9/2000 | Kanda |
| 6,241,675 | B1 | 6/2001 | Smith et al. |
| 6,246,895 | B1 | 6/2001 | Plewes |
| 6,312,382 | B1 | 11/2001 | Mucci et al. |
| 6,352,507 | B1 | 3/2002 | Torp et al. |
| 6,508,768 | B1 | 1/2003 | Hall et al. |
| 6,537,217 | B1 | 3/2003 | Bjærum et al. |
| 6,537,221 | B2 | 3/2003 | Criton et al. |
| 6,671,541 | B2 | 12/2003 | Bishop et al. |
| 6,683,454 | B2 | 1/2004 | Rehwald et al. |
| 6,685,641 | B2 | 2/2004 | Liu |
| 6,875,176 | B2 | 4/2005 | Mourad et al. |
| 7,055,378 | B2 | 6/2006 | Su et al. |
| 7,257,244 | B2 | 8/2007 | Miga |
| 7,331,926 | B2 | 2/2008 | Varghese et al. |
| 7,421,101 | B2 | 9/2008 | Georgescu et al. |
| 7,601,122 | B2 | 10/2009 | Zagzebski et al. |
| 7,753,847 | B2 | 7/2010 | Greenleaf et al. |
| 8,029,444 | B2 | 10/2011 | Pedrizzetti et al. |
| 2002/0065461 | A1 | 5/2002 | Cosman |
| 2002/0157472 | A1 | 10/2002 | Stephens et al. |
| 2003/0220556 | A1 | 11/2003 | Porat et al. |
| 2004/0006266 | A1 | 1/2004 | Ustuner et al. |
| 2004/0059224 | A1 | 3/2004 | Varghese et al. |
| 2004/0092816 | A1 | 5/2004 | Ossmann et al. |
| 2004/0210136 | A1 | 10/2004 | Varghese et al. |
| 2004/0215075 | A1 | 10/2004 | Zagzebski et al. |
| 2004/0249580 | A1 | 12/2004 | Pourcelot et al. |
| 2005/0004466 | A1 | 1/2005 | Hynynen et al. |
| 2005/0054930 | A1 | 3/2005 | Rickets et al. |
| 2005/0059876 | A1 | 3/2005 | Krishnan et al. |
| 2005/0080336 | A1 | 4/2005 | Byrd et al. |
| 2005/0267695 | A1 | 12/2005 | German |
| 2006/0058673 | A1 | 3/2006 | Aase et al. |
| 2006/0074315 | A1 | 4/2006 | Liang et al. |
| 2006/0173320 | A1 | 8/2006 | Radulescu |
| 2007/0016031 | A1 | 1/2007 | Mourad et al. |
| 2007/0049824 | A1 | 3/2007 | Konofagou et al. |
| 2007/0219447 | A1 | 9/2007 | Kanai et al. |
| 2007/0276242 | A1* | 11/2007 | Konofagou ............ 600/437 |
| 2007/0276245 | A1 | 11/2007 | Konofagou |
| 2008/0194957 | A1 | 8/2008 | Hoctor et al. |
| 2008/0269606 | A1 | 10/2008 | Matsumura |
| 2008/0285819 | A1 | 11/2008 | Konofagou et al. |
| 2008/0287792 | A1 | 11/2008 | Bae et al. |
| 2009/0149750 | A1 | 6/2009 | Matsumura |
| 2010/0138163 | A1* | 6/2010 | Gallippi et al. ............ 702/19 |
| 2011/0208038 | A1 | 8/2011 | Konofagou et al. |
| 2011/0245678 | A1* | 10/2011 | Tamura ............ A61B 8/08 600/453 |

OTHER PUBLICATIONS

Lazebnik, Roee. "Tissue Strain Analytics: Virtual Touch Tissue Imaging and Quantification." Siemens. Oct. 2008. pp. 1-5 (plus cover and back page).*

International Search Report and Written Opinion for International Application No. PCT/US11/38798.

Maleke et al., "Harmonic Motion Imaging for Focused Ultrasound (HMIFU): Initial In Vivo Results", 2009 IEEE International Ultrasonics Symposium Proceedings.

Maleke et al., "Real-Time Monitoring of Regional Tissue Elasticity During FUS Focused Ultrasound Therapy Using Harmonic Motion Imaging", AIP Conference Proceedings 829, pp. 171-175 (2006).

Vappou et al., "Pulse Wave Imaging for Noninvasive and Quantitative Measurement of Arterial Stiffness In Vivo", American Journal of Hypertension, vol. 23, No. 4, pp. 393-398, Apr. 2010.

Wang et al., "A composite imaging technique for high frame-rate and full-view cardiovascular ultrasound and elasticity imaging", Proceedings of the IEEE International Ultrasonics Symposium (New York, NY, USA), Oct. 28 to 31, 2007.

Shan et al., "A mechanical model to compute elastic modulus of tissues for harmonic motion imaging", Journal of Biomechanics, 41 (2008), pp. 2150-2158.

Ophir et al., "Elastography: ultrasonic estimation and imaging of the elastic properties of tissues", Proc. Instn. Mech. Engrs., vol. 213, Part H., 1999, pp. 203-233.

Konofagou et al., "Poroelastography: Imaging the Poroelastic Properties of Tissues", Ultrasound in Med. & Biol., vol. 27, No. 10, pp. 1387-1397, 2001.

Ophir et al., "Elastography: Imaging the Elastic Properties of Soft Tissues with Ultrasound", J Med Ultrasonics, Winter 2002, vol. 29, 2002, pp. 155-171.

Konofagou, "Quo vadis elasticity imaging?", Ultrasonics, 42 (2004), pp. 331-336.

Fung-Kee-Fung et al, "Angle-independent strain estimation in myocardial elastography", 4th International Tissue Elasticity Conference (Austin, TX, USA), Oct. 17 to 20, 2005.

Duck, "Physical properties of tissue: a comprehensive reference book. 1990 Academic Press," London, UK.

Jensen et al., "Calculation of pressure fields from arbitrarily shaped, apodized, and excited ultrasound transducers," IEEE Transactions on Ultrasonics, Ferroelectrics and Frequency Control, vol. 39(2), pp. 262-267, Mar. 1992.

Mitri et al., "Chirp imaging vibro-acoustography for removing the ultrasound standing wave artifact," IEEE transactions on medical imaging, vol. 24(10), pp. 1249-1255, Oct. 2005.

Bers, "Cardiac excitation-contraction coupling", Nature, Jan. 10, 2002, vol. 415:198-205.

Ramanathan et al., (2004) "Noninvasive electrocardiographic imaging for cardiac electrophysiology and arrhythmia," Nat Med 10(4):422-428.

Berger et al., (2006) "Single-Beat Noninvasive Imaging of Cardiac Electrophysiology of Ventricular Pre-Excitation. Journal of the American College of Cardiology," 48(10):2045-2052.

Greenstein et al., (2006) "Mechanisms of Excitation-Contraction Coupling in an Integrative Model of the Cardiac Ventricular Myocyte," Biophysical Journal 90:77-91.

Rice et al., "Approximate model of cooperative activation and crossbridge cycling in cardiac muscle using ordinary differential equations," Biophys. J 95:2368-2390, Sep. 2008.

Campbell et al., "Mechanisms of transmurally varying myocyte electromechanics in an integrated computational model," Phl. Trans. R. Soc. A., 366:3361-3380, Jul. 1, 2008.

Gurev et al., "Distribution of Electromechanical Delay in the Heart: Insights from a Three-Dimensional Electromechanical Model," Biophysical Journal 99:745-754, Aug. 2010.

Badke et al., (1980) "Effects of ventricular pacing on regional left ventricular performance in the dog," Am J Physiol Heart Circ Physiol 238:H858-867.

Wyman et al., (1999) "Mapping propagation of mechanical activation in the paced heart with MRI tagging," Am J Physiol Heart Circ Physiol 276:H881-891.

Prinzen et al., (1992) "The time sequence of electrical and mechanical activation during spontaneous beating and ectopic stimulation," Eur Heart J 13:535-543.

Provost et al., (2010) "Electromechanical Wave Imaging of Normal and Ischemic Hearts in Vivo," IEEE Trans. Med. Imaging 29(3):625-635.

Shehata et al., (2009) "Myocardial tissue tagging with cardiovascular magnetic resonance," Journal of Cardiovascular Magnetic Resonance 11:55.

(56) References Cited

OTHER PUBLICATIONS

Pernot et al., (2007) "ECG-gated, Mechanical and Electromechanical Wave Imaging of Cardiovascular Tissues In Vivo," Ultrasound in Medicine & Biology 33(7):1075-1085.
Provost et al., (2008) in 2008 IEEE International Ultrasonics Symposium (Beijing, China).
Durrer et al. (1970) "Total Excitation of the Isolated Human Heart. Circulation," 41:899-912.
Sengupta et al., (2008) "Electromechanical activation sequence in normal heart," Heart Fail Clin. 4:303-14.
Scher et al., (1956) "The pathway of ventricular depolarization in the dog," Circ. Res 4:461-469.
Faris et al. (2003) "Novel Technique for Cardiac Electromechanical Mapping with Magnetic Resonance Imaging Tagging and an Epicardial Electrode Sock," Ann Biomed Eng. 31:430-440.
Gurev et al., (2009) "In silico characterization of ventricular activation pattern by electromechanical wave imaging," Supplement to Heart Rhythm 6:S357.
Ramanathan et al., "Activation and repolarization of the normal human heart under complete physiological conditions," Proceedings of the National Academy of Sciences 103(16):6309-6314, Apr. 18, 2006.
Lee et al., "Theoretical Quality Assessment of Myocardial Elastography with In Vivo Validation," Ultrasonics, Ferroelectrics and Frequency Control, IEEE Transactions on 54(1):2233-2245, Nov. 11, 2007.
Kimber et al. (1996) "A Comparison of Unipolar and Bipolar Electrodes During Cardiac Mapping Studies," Pacing Clin Electro 19:1196-1204.
Kallel et al., (1997) "A least-squares strain estimator for elastography," Ultrason Imaging 19:195-208.
Luo et al., "High-frame rate, full-view myocardial elastography with automated contour tracking in murine left ventricles in vivo," IEEE Transactions on Ultrasonics, Ferroelectrics and Frequency Control, 55(1):240-248, Jan. 2008.
Lai et al., (1993) "Introduction to Continuum Mechanics," (Pergamon Pr). 3rd Ed., Contents.
Stewart et al., "Blood-eye barriers in the rat: Correlation of ultrastructure with function," J. Comp. Neurol., vol. 340, No. 4, pp. 566-576, 1994.
Samuel et al., "An ex vivo study of the correlation between acoustic emission and microvascular damage," Ultrasound Med. Biol., vol. 35, No. 9, pp. 1574-1586, 2009.
Luo et al., "Pulse wave imaging of normal and aneurysmal abdominal aortas in vivo", IEEE Trans. Med. Imaging 28(4): 477-486, 2009.
Luo et al., "A fast normalized cross-correlation method for motion estimation," IEEE Trans. Ultrason. Ferroelectr. Control 57(6): 1347-1357, Jun. 2010.
Maleke et al., "Single-Element focused Ultrasound Transducer Method for Harmonic Motion Imaging," Ultrason. Imaging, vol. 28, No. 3, pp. 144-158, 2006.
Maleke et al., "In Vivo Feasibility of Real-time Monitoring of Focused Ultrasound Surgery (FUS) Using Harmonic Motion Imaging (HMI)," IEEE Trans. Biomed. Eng., vol. 57(1), pp. 7-11, Jan. 2010.
Ophir et al., "Elastography: A quantitative method for imaging the elasticity of biological tissues," Ultrasonic Imaging, vol. 13(2), pp. 111-134, 1991.
Huang et al., "Watershed Segmentation for Breast Tumor in 2-D Sonography," May 2004, Ultrasound in Medicine and Biology, pp. 625-632.
Chang et al., "3-D US Frame Positioning Using Speckle Decorrelation and Image Registration," Jun. 2003, Ultrasound in Medicine and Biology, pp. 801-812.
Luo et al., "Myocardial elastography at both high temporal and spatial resolution for the detection of infarcts," Ultrasound in Med. & Bio, vol. 33(8), pp. 1206-1223, Aug. 2007.

Wang et al., "A composite high frame-rate system for clinical cardiovascular imaging," IEEE Transactions on Ultrasonics, Ferroelectrics, and Frequency Control, vol. 55(10), pp. 2221-2233, Oct. 2008.
Kanai, "Propagations of spontaneously actuated pulsive vibration in human heart wall and in vivo viscoelasticity estimation," IEE Transaction on Ultrasonics, Ferroelectrics, and Frequency Control, vol. 52(11), pp. 1931-1942, Nov. 2005.
Bercoff et al., "Supersonic Shear Imaging: A new technique for soft tissue elasticity mapping," IEEE Transactions on Ultrasonics, Ferroelectrics, and Frequency Control, vol. 51(4), pp. 396-409, Apr. 2004.
McLaughlin et al., "Piezoelectric sensor determination of arterial pulse wave velocity," Physiol. Meas., vol. 24(3), pp. 693-702, 2003.
Greenwald, "Pulse pressure and arterial elasticity," QJM: An International Journal of Medicine, vol. 95(2), pp. 107-112, 2002.
Kanai et al., "Myocardial rapid velocity distribution," Ultrasound Med. & Biol., vol. 27(4), pp. 481-498, Apr. 2001.
Rogers et al., "Age-associated changes in regional aortic pulse wave velocity," J Am Coll. Cardiol., vol. 38(4), pp. 1123-1129, 2001.
Declerck et al., "Left ventricular motion reconstruction from planar tagged MR images: a comparison," Phys. Med. Biol., vol. 45(6), pp. 1611-1632, Jun. 2000.
Kanai et al., "Transcutaneous measurement of frequency dispersion in the regional pulse wave velocity," IEEE Ultrasonics Symposium, 2000.
Sinkus et al., "High-resolution tensor MR elastography for breast tumor reduction," Phys Med Biol, 2000, 45(6): 1649-1664.
Roth, "Influence of a perfusing bath on the foot of the cardiac action potential," Circulation Research, vol. 86, E19-E22, 2000.
Wang et al., "Increased aortic stiffness assessed by pulse wave velocity in apolipoprotein E-deficient mice," Am J Physiol Heart Circ. Physiol., vol. 278, No. 2, pp. H428-H434, 2000.
Sandrin et al., "Time-resolved pulsed elastography with ultrafast ultrasonic imaging," Ultrason Imaging, vol. 21(4), pp. 259-272, 1999.
Cutnell et al., Physics, Fourth Edition, New York. Table of Contents, 1998.
Heimdal et al., "Real-time strain rate imaging of the left ventricle by ultrasound," J Am Soc. Echocardiog., vol. 11(11), pp. 1013-1019, 1998.
Konofagou et al., "A New Elastographic Method for Estimation and Imaging od Lateral Strains, Corrected Axial Strains and Poison's Ratios in Tissues," Ultrasound in Medicine & Biology 24(8): 1183-1199, 1998.
Konofagou et al., "Three-dimensional Motion estimation in Elastography," IEEE Proceedings of the Symposium of Ultrasonics, Ferroelectrics, and Frequency Control in Sendai Japan, pp. 1745-4178, vol. 2, 1998.
Nichols et al., "Vascular Impedance. In McDonald's: blood flow in arteries: theoretical, experimental, and clinical principles," E Arnold, London, 1998. Table of Contents.
Sarvazyan et al., "Shear wave elasticity imaging: A new ultrasonic technology of medical diagnostics," Ultrasound Med Biol, vol. 24(9), pp. 1419-1435, Nov. 1998.
Spach et al., "Extracellular discontinuities in cardiac muscle—Evidence for capillary effects on the action potential foot," Circulation Research, vol. 83, pp. 1144-1164, 1998.
Sutherland, "Color Doppler Myocardial Imaging—Potential Applications in Acquired and Congenital Heart Disease," Acta Paediatr, 84: pp. 40-48, Aug. 1995.
Walker et al., "A Fundamental Limit on Delay Estimation Using Partially Correlated Speckle Signals," IEEE T Ultrason Ferr, vol. 42(2), pp. 301-308, Mar. 1995.
Gupta, et al., "Changes in Passive mechanical Stiffness of Myocardial Tissue with Aneurysm Formation," Circulation, vol. 89, pp. 2315-2326, 1994.
Fung, "Biomechanics—Mechanical Properties of Living Tissues," New York, 1993, Table of Contents.
Kanai, et al., "A New Method for Measuring Small Local Vibrations in the Heart Using Ultrasound," IEEE T Bio-Med Eng, vol. 40(12), pp. 1233-1242, Dec. 1993.

(56) References Cited

OTHER PUBLICATIONS

Zerhouni, et al., "Human Heart: tagging with MR imaging—a method for noninvasive assessment of myocardial motion," Radiology 169(1): 59-63, Oct. 1988.
Bonnefous, et al., "Time domain formulation of pulse-Doppler ultrasound and blood velocity estimation by cross-correlation," Ultrason Imaging, vol. 8(2), pp. 73-85, Apr. 1986.
Avolio, et al., "Effects of aging on changing arterial compliance and left ventricular load in a northern Chinese urban community," Circulation, vol. 68(1), pp. 50-58, 1983.
Edwards, et al., "Effects of Ischemia on Left-Ventricular Regional Function in the Conscious Dog," American Journal of Physiology, vol. 240, pp. H413-H420, 1981.
Henderson, et al., "Series Elasticity of Heart Muscle During Hypoxia," Cardiovascular Research, vol. 5, pp. 10-14, 1971.
Konofagou et al., "Myocardial Elastography—Feasibility Study in Vivo," Ultrasound Med & Biol, vol. 28(4), pp. 475-482, Apr. 2002.
McNally et al., "Computer Vision Elastography: Speckle Adaptive Motion Estimation for Elastography Using Ultrasound Sequences." IEEE Transactions on Medical Imaging, vol. 24, No. 6, pp. 755-766 (2005).
Zheng, et al., "High Resolution ultrasound elastomicroscopy imaging of soft tissues: system development and feasibility; Ultrasound elastomicroscopy," Physics in Medicine and Biology, vol. 49, No. 17, pp. 3925-3938 (Sep. 7, 2004).
Chen et al., "Estimation of Displacement Vectors and Strain Tensors in Elastography Using Angular Insonifications." IEEE Transactions on Medical Imaging, vol. 23, No. 12, pp. 1479-1489 (Dec. 1, 2004).
Konofagou et al., "Elastographic Imaging of the Strain Distribution at the Anterior Cruciate Ligament and ACL-Bone Insertions" 27th Annual International Conference of the Engineering in Medicine and Biology Society, pp. 972-975 (Shanghai, China Sep. 1-4, 2005).
Qin et al., "The Natural Frequency of Nonlinear Oscillation of Ultrasound Contrast Agents in Microvessels," Ultrasound in Med. & Biol., vol. 33, No. 7, pp. 1140-1148, 2007.
Konofagou et al., "Noninvasive Electromechanical Wave Imaging and Conduction Velocity Estimation in Vivo," Ultrasonics Symposium, 2007 IEEE, pp. 969-972, 2007.
Konofagou et al., "Electromechanical Wave imaging for noninvasive mapping of the 3D electrical activation sequence in canines and humans in vivo,"Journal of Biomechanics, 45(5):856-864 (Mar. 15, 2012).
Otani et al., "Transmural ultrasound-based visualization of patterns of action potential wave propagation in cardiac tissue," Annals Biomedical Engineering, 38(10):3112-3123 (2010).
Chen et al., "Architectural Acoustics and Noise: Advancements and Best Practices in Instrumentation for Architectural Acoustics and Noise," J. Acoust. Soc. Am.; 164th Meeting: Acoustical Society of America, 132(3, Pt. 2):1977-2018 (Sep. 2012) Cited in IR Assessments: Chen, et al., Radiation-Force-Based Estimation of Acoustic Attenuation Using Harmonic Motion Imaging (HMI) in Phantoms and In Vitro Livers Before and After HIFU Ablation , Ultrasound in Medicine and Biology, Submitted and included in IR Report.
Chen et al., "Engineering Acoustics and ASA Committee on Standards: Sound Intensity Measurements," J. Acoust. Soc. Am.; 164th Meeting: Acoustical Society of America, 132(3, Pt. 2):1984 (Sep. 2012); Cited in IR Assessment as: Chen, et al., Radiation-Force-Based Estimation of Acoustic Attenuation Using Harmonic Motion Imaging (HMI) in Phantoms and In Vitro Livers Before and After HIFU Ablation, Ultrasound in Medicine and Biology, Submitted and included in IR Report.
Palmeri et al., "Characterizing Acoustic Attenuation of Homogeneous Media Using Focused Impulsive Acoustic Radiation Force," Ultrasonic Imaging, 28(2):114-128 (2006).
Duerinckx et al., "In vivo Acoustic Attenuation in Liver: Correlations with Blood Tests and Histology," Ultrasonic in Medicine & Biology, 14(5):405-413 (1988).
Fujii et al., "A New Method for Attenuation Coefficient Measurement in the Liver," Journal of Ultrasound in Medicine, 21(7):783-788 (2002).

Damianou et al., "Dependence of Ultrasonic Attenuation and absorption in dog soft tissues on Temperature and Thermal dose," The Journal of Acoustical Society of America, 102(1):628-634 (1997).
Techavipoo et al., "Temperature Dependence of Ultrasonic Propagation Speed and Attenuation in Excised Canine Liver Tissue Measured Using Transmitted and Reflected Pulses," The Journal of Acoustical Society of America, 115(6):2859-2865 (2004).
Papadakis, "Ultrasonic Instruments & Devices," Academic Press, 1999.
Cobbold, "Foundations of biomedical ultrasound," Biomedical engineering series, Oxford University Press, pp. 422-423(2006).
Jasaityte et al., "Current state of three dimensional myocardial strain estimation using echocardiography," Journal of the American Society of Echocardiography, 26(1):15-28 (2013).
Konofagou et al., "Noninvasive electromechanical wave imaging and conduction-relevant velocity estimation in vivo," Ultrasonics, 50(2):208-215 (2010).
Provost et al., "Imaging the electromechanical activity of the heart in vivo," Proceedings of the National Academy of Sciences, 108:8565-8570 (2011).
Provost et al., "Mapping of cardiac electrical activation with electromechanical wave imaging: An in silico-in vivo reciprocity study," Heart Rhythm, 8(5):752-759 (2011).
Otani et al., "Use of ultrasound imaging to map propagating action potential waves in the heart," Computers in Cardiology, 36:617-620 (2009).
Ginat et al., "High-resolution ultrasound elastography of articular cartilage in vitro," Proceedings of the 28th IEEE EMBS Annual International Conference, New York City, US App. 6644-6647 (Aug. 30-Sep. 3, 2006).
Zheng et al., "Ultrasonic measurement of depth-dependent transient behaviors of articular cartilage under compression," Journal of Biomechanics, 38:1830-1837 (2005).
Shinna et al., "Realtime tissue elasticity imaging using the combined autocorrelation method," J. Med. Ultrasonics, 29(autumn):119-128 (2002).
Borden et al., "Ultrasound Radiation Force Modulates Ligand Availability on Target Contrast Agents," Mol. Imaging, 5:139-147 (2006).
Vial (en.wikipedia.org/wiki/Vial) downloaded May 20, 2014.
European Search Report for EP Application No. EP 10838238, dated May 6, 2014.
International Search Report for PCT/US2011/34704.
Zwanenburg et al., (2004) "Timing of cardiac contraction in humans mapped by high-temporal-resolution MRI tagging: early onset and late peak of shortening in lateral wall," Am J Physiol Heart Circ Physiol 286:H1872-1880.
Walker et al., (1994) "A fundamental limit on the performance of correlation based phase correction and flow estimation techniques," Ultrasonics, Ferroelectrics and Frequency Control, IEEE Transactions on 41(5):644-654, Sep. 1994.
Pernot et al., "Electromechanical Imaging of the Myocardium at Normal and Pathological States", Ultrasonics Symposium, 2005 IEEE, pp. 1091-1094, 2005.
Fenster et al., "Three-dimensional ultrasound imaging," Physics in Medicine and Biology, 46(5):R67-R99 (2001).
De Craene et al., "Temporal diffeomorphic free-form deformation: Application to motion and strain estimation from 3D echocardiography," Medical Image Analysis, 16(2):427-450 (2012).
Housden et al., "Ultrasonic imaging of 3D displacement vectors using a simulated 2D array and beamsteering," Ultrasonics, 53(2):615-621 (2013).
DuBose et al., "Confusion and Direction in Diagnostic Doppler Sonography," Journal of Diagnostic Medical Sonography, 25(3):173-177 (2009).
Yuh, et. al., "Delivery of Systemic Chemotherapeutic Agent to Tumors by Using Focused Ultrasound: Study in a Murine Model," Radiology, 234(2): 431-437, 2005.
Tanter et al., "Ultrafast compound imaging for 2-D motion vector estimation: application to transient elastography," IEEE Trans Ultrason Ferroelectr Freq Control, vol. 49(10), pp. 1363-74, 2002.

(56) References Cited

OTHER PUBLICATIONS

Brooks et al., "Electrical Imaging of the Heart," IEEE Signal Processing Magazine, vol. 14(1), pp. 24-42, Jan. 1997.
Luo et al., "Myocardial elastography at both high temporal and spatial resolution for the detection of infarcts," Ultrasound Med. Biol. 33(8): 1206-1223, 2007.

* cited by examiner (a) General HMI setup, (b) actual distribution of the acoustic radiation force field, and (c) equivalent volumic force modeled as uniform within the focal region.

Summary of how the HMI modulus is calculated.

HMI modulus measured on polyacrylamide phantom versus Young's modulus measured by mechanical testing on the same gels.

Assumption of cylindrical focus, Forces acting on the cylinder

Axial strain fields around the focal region for both input force field profiles (a): Actual force field, (b): Corresponding force field modeled as being uniform within the focal region.

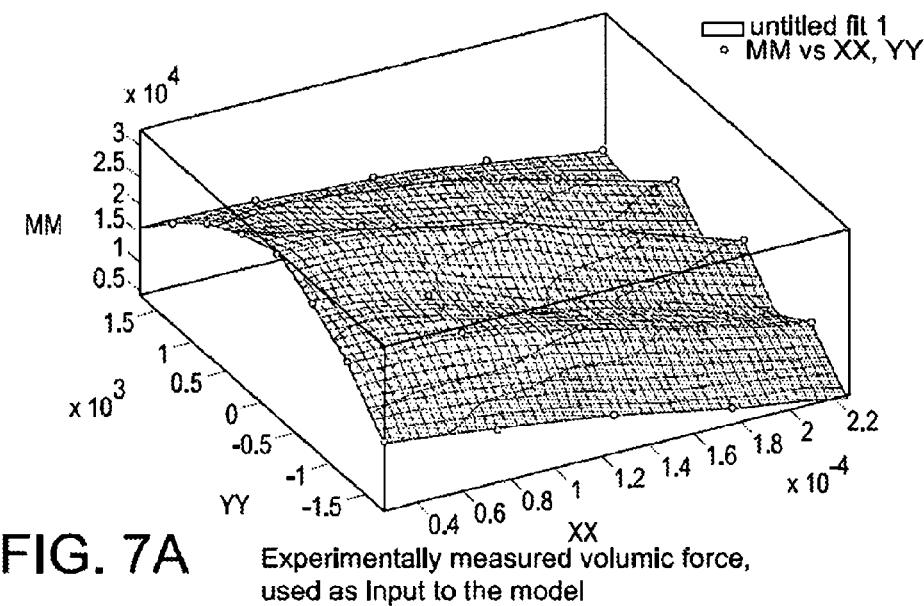
FIG. 7A  Experimentally measured volumic force, used as input to the model
FIG. 7B
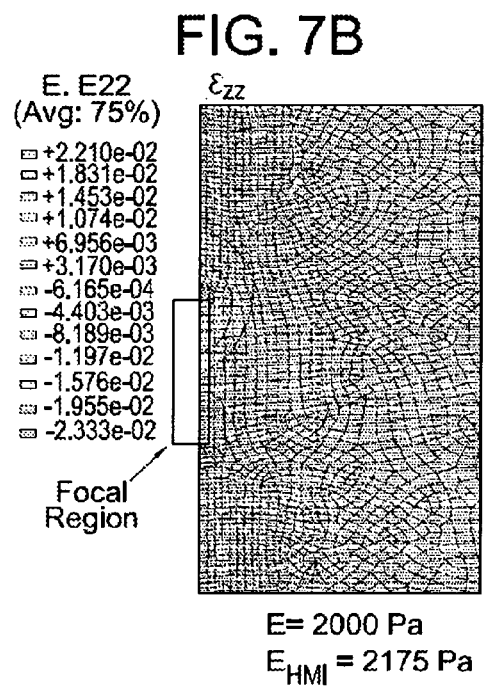
E= 2000 Pa
$E_{HMI}$ = 2175 Pa
FIG. 7C
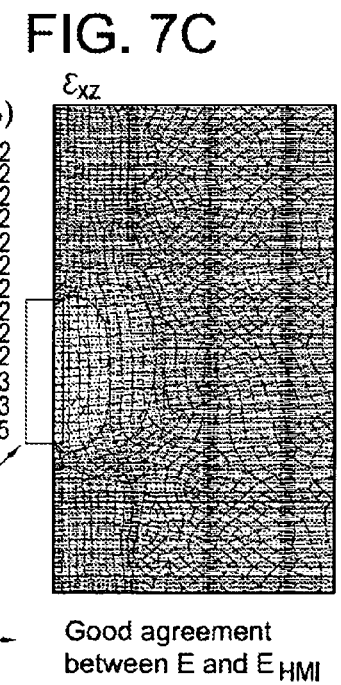
Good agreement between E and $E_{HMI}$ HMI modulus versus Young's modulus obtained in the numerical study.

HMI modulus obtained when focusing within inclusion in the case of the heterogeneous numerical phantom.

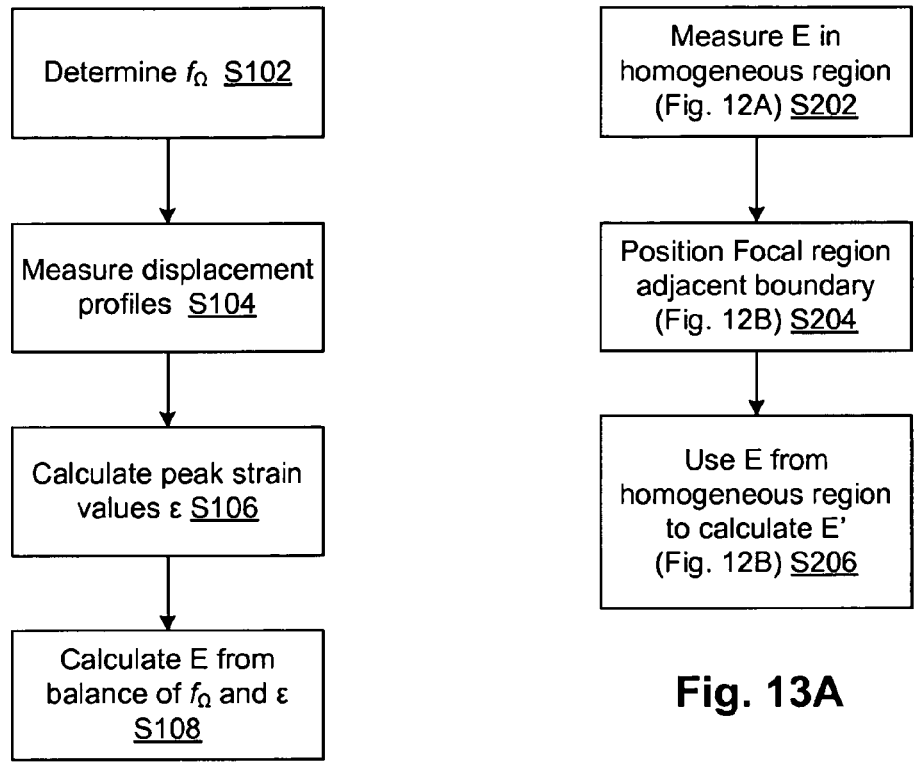

DEVICES, METHODS, AND SYSTEMS FOR MEASURING ELASTIC PROPERTIES OF BIOLOGICAL TISSUES USING ACOUSTIC FORCE

CROSS-REFERENCE TO RELATED APPLICATIONS

This application is a national stage entry of International Application No. PCT/US11/38798, filed Jun. 1, 2011, which claims priority to and the benefit of U.S. Provisional Application Nos. 61/427,169, filed on Dec. 24, 2010, and 61/350,369, filed on Jun. 1, 2010, both of which are incorporated herein by reference in their entireties.

STATEMENT REGARDING FEDERALLY SPONSORED RESEARCH

This invention was made with government support under Grant No. 1R21EB008521 awarded by National Institute of Health. The government has certain rights in this invention.

FIELD

The disclosed subject matter relates generally to systems and methods for noninvasively measuring mechanical properties of biological tissues and organs, and more particularly to systems and methods for using ultrasound energy to generate an internal force remotely to measure quantitatively tissue elasticity in vivo and non-invasively.

BACKGROUND

Elasticity Imaging is a known class of techniques for the estimation of mechanical properties of materials. In addition to diagnosis by palpation, methods have been proposed for elasticity imaging for biomechanics for measuring mechanical properties in vivo in a non invasive, non destructive manner.

Examples of the use of elasticity imaging methods for biomechanical applications include the use of Magnetic Resonance Elastography (MRE) for the determination of brain and liver tissue viscoelastic properties in vivo and comparison between in vivo and post-mortem brain properties, the use of MRE for the measurement of skeletal muscle contraction and muscle stiffness changes with aging, the use of Transient Elastography to assess skeletal muscle stiffness during contraction, or the use of Supersonic Shear Imaging (SSI) for the measurement of shear wave dispersion curves for characterization of soft tissue viscoelasticity.

Indentation is also a widely used material testing method that allows measuring the Load-Displacement curve. Analytical solutions are possible in the case of penetration of axisymetric indenters in an elastic half space. It is possible to derive the Young's modulus of the tested material, for example, by estimation using a complex iterative procedure and calibration process. While indentation is commonly used for materials such as polymers and metallic samples, the application of such an experimental approach is limited in in vivo contexts, due to the intrinsic limitations of indentation such as the need to apply forces externally or using invasive mechanisms.

Conventional quantitative mechanical testing methods are generally performed externally and, in operation, consist of using an actuator (e.g., a piston) that imposes a controlled force on the subject tissue. The mechanical response of the tissue is measured subsequently, allowing an estimate of the mechanical properties of the tested sample. Since the actuator is in contact with the subject tissue, such methods are limited to external testing. Presently, internal testing methods can be performed invasively.

SUMMARY

Disclosed embodiments include systems and methods for measuring mechanical properties of biological samples, such as tissues and organs, in vivo in a non-invasive and non-destructive manner.

Disclosed embodiments include systems and methods for measuring in vivo and non-invasively tissue elasticity based on the principle of indentation.

Disclosed embodiments include non-invasive internal indentation systems and methods that use acoustic radiation force resulting from focused ultrasound energy and simultaneously measure the effect of the acoustic radiation force exerted on the tissue.

Disclosed embodiments include systems and methods that use the acoustic radiation force resulting from focused ultrasound in order to generate an internal force in tissue remotely and to quantitatively measure the effect of the applied force on the tissue.

Disclosed embodiments include systems and methods using the principles of a Harmonic Motion Imaging (HMI) method.

Disclosed embodiments include systems and methods for measuring elastic properties of, for example tissues in a living host, non-invasively by using internal indentation using features of the Harmonic Motion Imaging method (HMI).

Disclosed embodiments include systems and methods for an HMI-based mechanical testing setup that is particularly relevant for biomechanics as it is non-contact, non-invasive, and it can be used in vivo.

Disclosed embodiments include systems and methods for quantitative measurement of the HMI elastic modulus $E_{HMI}$ and estimation of the actual Young's modulus (E) based on the correlation between $E_{HMI}$ and Young's modulus E.

Disclosed embodiments include systems and methods for non-invasive, non-destructive, remote measurements enabling internal tissue to be tested at deep locations within a subject. The methods, devices, and systems are not limited to surface tissue and are therefore applicable for in vivo testing.

Disclosed systems and methods include an all-in-one tool for tumor detection, characterization, targeting and monitoring of thermal ablation.

Disclosed embodiments include a device, method, and system for using the acoustic radiation force resulting from focused ultrasound in order to generate an internal force remotely (which can be represented as an "internal" piston) and to measure quantitatively tissue elasticity in vivo and non-invasively. For this purpose, two ultrasound transducers may be employed. A first of the two may include a Focused Ultrasound (FUS) transducer, and a second of the two may include an imaging transducer. The FUS may generate an ultrasound wave at a predetermined frequency and may be amplitude modulated to generate an acoustic radiation force, oscillating at twice the modulation frequency, at its focus region. The imaging transducer may be confocal and concentric with the FUS transducer. The imaging transducer may be configured to receive the energy from a region around the focus region. Image data is captured by the imaging transducer at a frame rate, for example, in the range of 100-200 Hz.

A processor may be used to convert acquired sequences of image data to displacement data and to derive associated tissue properties. Tissue properties may include Young's modulus. The transducers may be inserted in the body of a living host through a natural or artificial passage to measure tissue properties at a point remote from the passage. The transducers may be placed on the body of a living host to measure tissue properties at a point remote from the point of placement. The processor may be used to control the acquisition of data and the generation of ultrasound radiation force.

Embodiments of the disclosed subject matter include systems configured to implement the methods described as well as devices, components, and articles of manufacture for implementing the methods.

BRIEF DESCRIPTION OF THE DRAWINGS

FIG. 7A is a graph of an experimentally measured volumic force;

FIGS. 7B and C illustrate correlations between measured elastic modulus and Young's modulus;

FIG. 12 is a flow chart of a method for determining an elastic property of a region of a material with homogeneous elastic properties according to embodiments of the disclosed subject matter;

FIG. 13A is a flow chart of a method of determining an elastic property of a region of a material with inhomogeneous elastic properties according to embodiments of the disclosed subject matter; and FIGS. 13B and 13C illustrate the calculation corresponding to methods of FIGS. 12 and 13A, respectively.

DETAILED DESCRIPTION OF THE DRAWINGS

Figure 1:
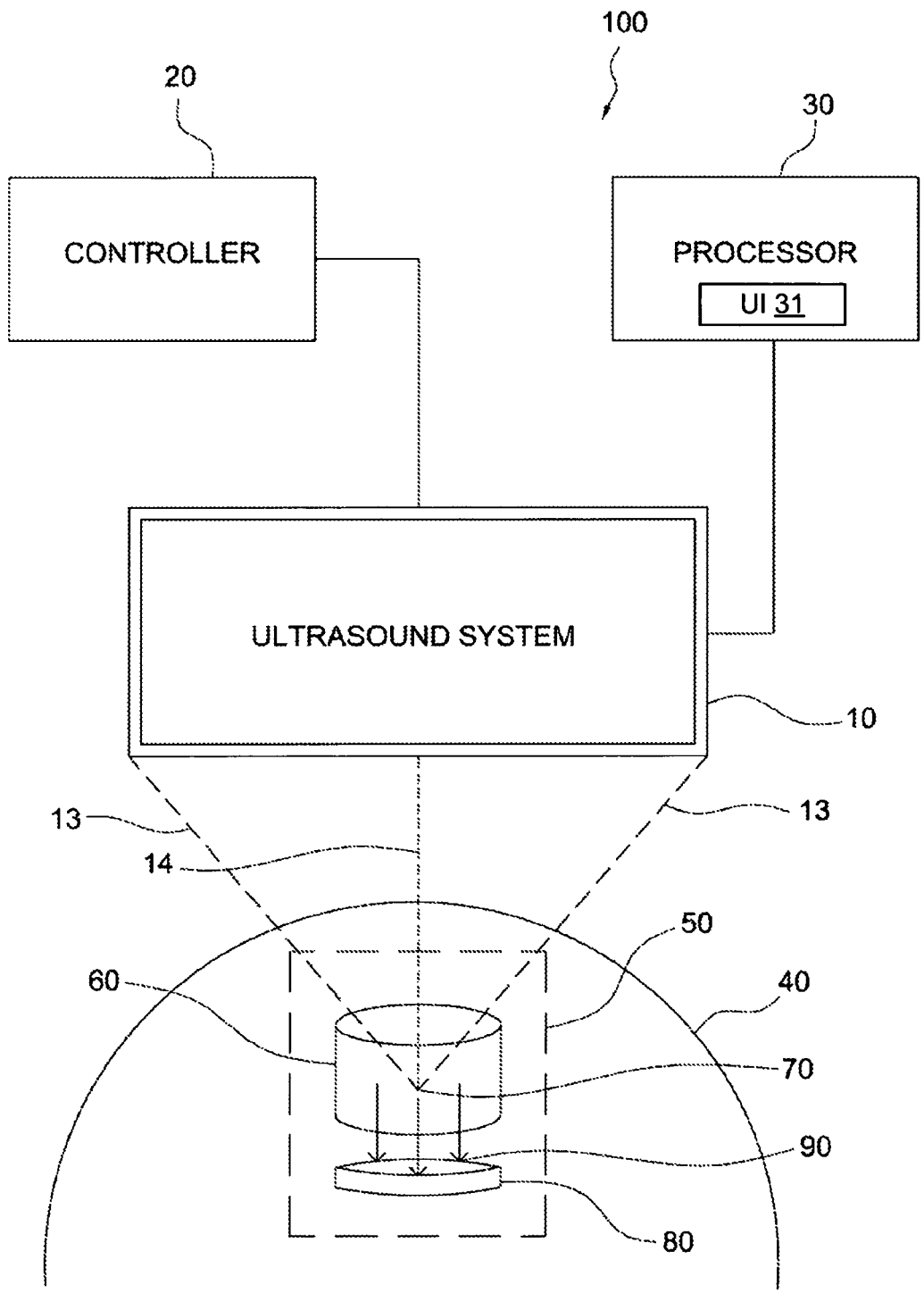
FIG. 1 is a quasi-schematic representation of a system for measuring mechanical properties of biological tissues according to some embodiments of the disclosed subject matter.

Measuring material properties with noninvasive, nondestructive methods in biological tissues presents unique challenges. Conventional mechanical testing methods may be external and thereby limited to either superficial tissue in vitro testing or invasive testing. These methods may not allow measurement of mechanical properties of major organs in vivo. Measuring non-invasively in vivo mechanical properties of tissues in their natural physiological environment is particularly challenging in the biomechanics field. Furthermore, since a large number of pathologies result in a significant alteration of mechanical properties, the latter can be used as contrast for diagnostic purposes. This is the basis of palpation as well as research in the field of elasticity imaging.

A general objective of the disclosed systems and methods is to provide a Harmonic Motion Imaging (HMI)-based mechanical testing system and method that is suitable for biomechanics as it is non-contact, non-invasive, and it can be used in vivo. Harmonic Motion Imaging (HMI) is an ultrasound-based method that uses an amplitude modulated signal in order to generate an oscillating radiation force at the focal region of the target sample. Within the small focal region (typically 4 mm×1 mm), a volumic force oscillates at a single frequency within typically the 10-200 Hz range. At the same time, an imaging transducer is used to acquire raw ultrasound (RF) data from a region surrounding the focal region. Displacements resulting from the oscillating acoustic radiation force are estimated from the image data using cross-correlation techniques. This method thus, relies on a principle that is similar to indentation techniques, but uses the localized, internal acoustic radiation force where an external mechanical indenter might otherwise be used to generate stress.

Disclosed embodiments therefore include non-invasive internal indentation systems and methods that use the acoustic radiation force resulting from focused ultrasound energy (beam) to internally displace (indent) the sample while simultaneously measuring the resulting displacement. The acoustic radiation force resulting from the focused ultrasound can thus be used to generate an internal force in tissue remotely.

Disclosed embodiments further include systems and methods for measuring elastic properties of, for example tissues in a living host, non-invasively by using internal indentation using features of the Harmonic Motion Imaging method (HMI). The described methods employ the oscillating acoustic radiation force produced by a focused ultrasound transducer (FU) at the focal region. The acoustic radiation force may be used for internal, non-contact indentation of soft tissues. The resulting displacements can be measured using a concentric, confocal ultrasound imaging transducer. By estimating the applied force and by measuring the resulting displacements and subsequent deformations, a stiffness modulus namely, an HMI modulus $E_{HMI}$, can be calculated. $E_{HMI}$ differs from the Young's modulus E by definition. However, studies have shown on both numerical and physical phantoms that the correlation between these two moduli is very high. Hence, the HMI modulus $E_{HMI}$ conveys full information on local linear elastic properties.

Since the HMI elastic modulus (stiffness index) $E_{HMI}$ is defined as the stress imposed by the piston on the underlying tissue divided by the measured uniaxial strain, and it is equal to the ratio between the applied stress and the resulting uniaxial strain, the HMI elastic modulus $E_{HMI}$ can be calculated from the axial and shear strain values measured around the focal region. Since there is a good correlation between the HMI modulus $E_{HMI}$ and the actual Young's modulus E, this system allows for quantitative measurements of the actual Young's modulus E. This system and method therefore allows to quantitatively measure tissue elasticity in vivo and non-invasively. The measurement of E using this method is robust, reproducible and localized, and is strongly independent of boundary conditions and sample geometry.

A further objective of the HMI system and method is to constitute an all-in-one tool for tumor detection, characterization, targeting and monitoring of the thermal ablation.

Additional objectives include investigation of a new role for HMI, namely, a mechanical testing tool, where a known dynamic force is applied on a target sample, the resulting displacement is measured, and a mechanical property of the target sample is derived from the measured displacement and the known applied force.

Furthermore, embodiments are disclosed to (1) propose a stiffness index, namely, an HMI modulus $E_{HMI}$, based on the applied force and the measured strains; (2) evaluate the correlation between $E_{HMI}$ and the true Young's modulus E with finite-element simulations; and (3) evaluate to quality and the experimental feasibility of the proposed method on phantoms, by comparing $E_{HMI}$ to the Young's modulus measured by mechanical testing.

Figure 2:
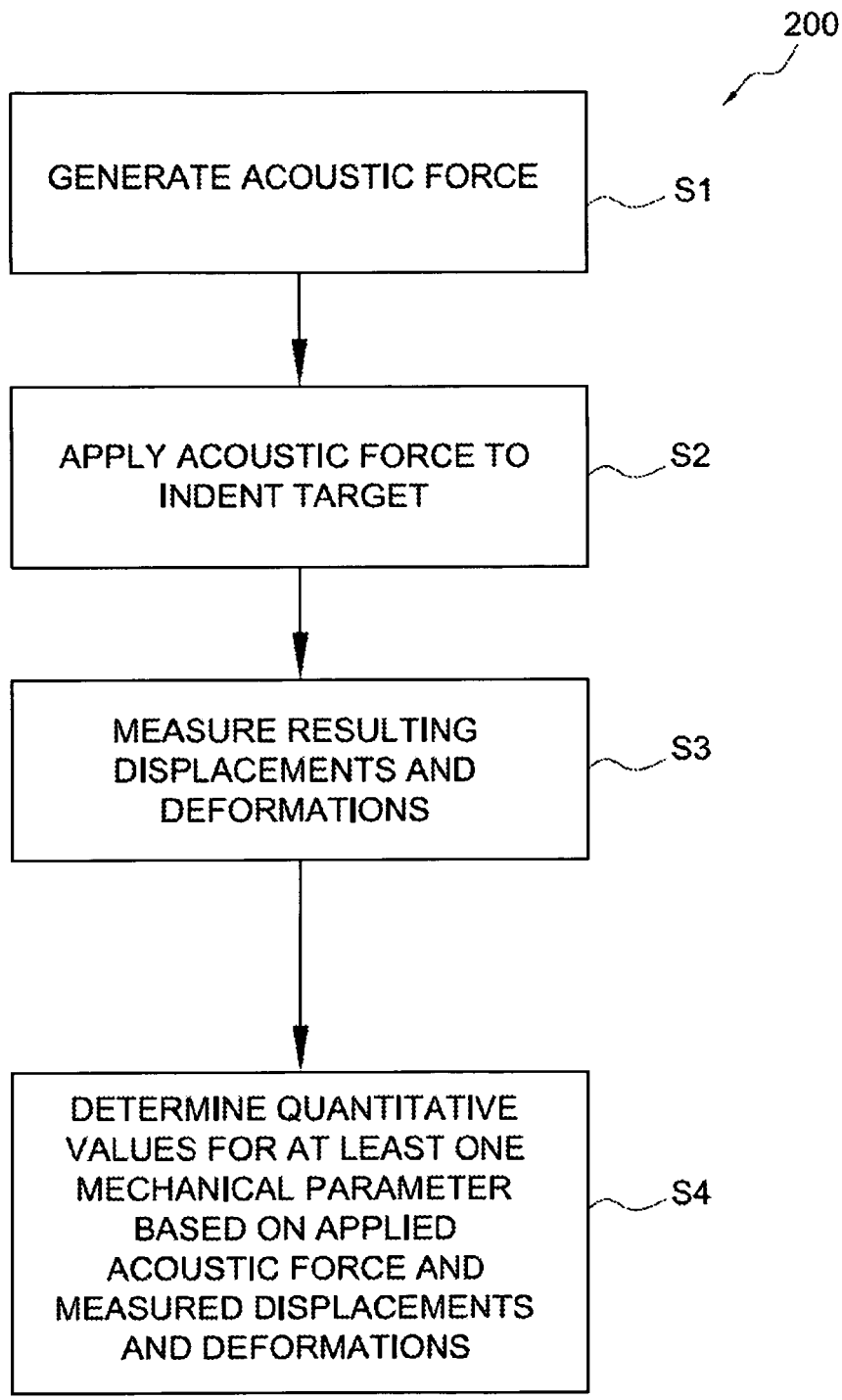
FIG. 2 is a flow chart of an exemplary method for determining a parameter of a mechanical property according to embodiments of the disclosed subject mater.
Figure 3:
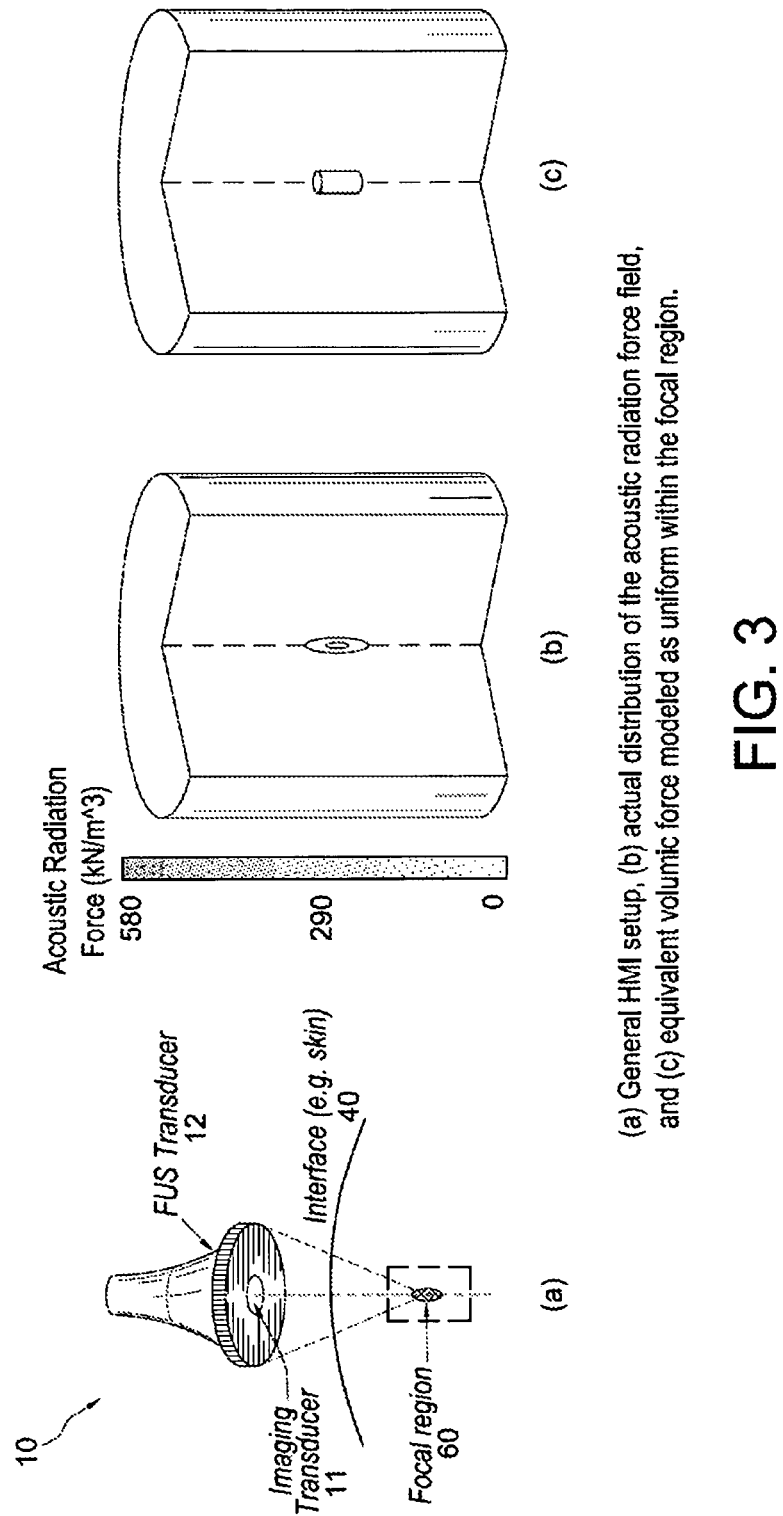
FIG. 3(a) is a schematic representation of a general Harmonic Motion Imaging system.
FIG. 3(b) is a representation of an actual distribution of an acoustic radiation force field.
FIG. 3(c) is a representation of an equivalent volumic force modeled as uniform within a focal region.

Referring now to FIGS. 1, 2, and 3, FIG. 1 shows an exemplary system 100 that can be used to remotely and non-invasively measure mechanical properties, such as elasticity, of a tissue or organ situated deep within a subject. The system 100 includes an ultrasound system 10 to generate remotely an oscillating force at a focal region 60 of a target sample 50 located within a subject at a location below an interface, such as the skin of the subject, 40 and to acquire image sequences of the focal region 60. As shown in FIG. 3, ultrasound system 10 includes a focused ultrasound (FUS) transducer 12, and an imaging transducer 11, the imaging transducer 11 being confocal and concentric with the FUS transducer 12. In alternative embodiments, the FUS transducer may be located remotely from the imaging transducer or adjacent the imaging transducer or overlapping the imaging transducer. The transducers 11 and 12 may be inserted in the body of a living host through a natural or artificial passage to measure tissue properties at a point remote from the passage. The transducers 11, 12 may also be placed on the body of a living host to measure tissue properties at a point remote from the point of placement.

The focused ultrasound (FUS) transducer generates an oscillating force at a focal region 60. To generate such a force, a high frequency ultrasonic signal (f=4.5 MHz, for example) is amplitude-modulated by a low frequency signal (f=5-100 Hz, for example) by a controller 20 and the ultrasound beam 13 is focused at a focal point 70 within the focal region 60. This results in a volumic acoustic radiation force F (shown in FIG. 4) oscillating at twice the amplitude modulation (AM) frequency. The focal region 60 can thus be considered to act as a "rigid piston" that exerts an oscillating internal force F to the underlying (tissue) region 80. The resulting displacement 90 of the tissue region 80 is measured using consecutive (RF) signals acquired by the imaging transducer 11.

The imaging transducer 11 can be a phased array operating at, for example, a frequency of f=3.3 MHz, or a pulse-echo transducer operating at a frequency of f=7.5 MHz, for example. Being co-located, (e.g., concentric and confocal) with the focused ultrasound transducer (FUS) 12 the imaging transducer 11 may be positioned to induce motion and simultaneously receive the raw ultrasound (RF) data from region 80 of the tissue from a single device. The application of force and the imaging of the resulting motion may be done simultaneously in time by the respective transducers.

Using a high beam density 14 and a reduced sector size, this raw ultrasound data is used to image the underlying tissue region 80 with high spatial resolution at a high frame rate (100 Hz-400 Hz, for example). In sum, the (FUS) transducer 12 generates a force F inside the tissue while the imaging transducer 11 simultaneously measures the effect of this force F (e.g., displacements and subsequently deformations). In operation, the FUS transducer 12 generates and applies (S1) an acoustic force F to remotely indent a target tissue (S2) located deep within a subject. The imaging transducer 11 captures sequences of image data of the indented target tissue which images are then processed by a processor 30 to estimate/measure (S3) the resulting displacements and deformations of the indented target tissue. The measured displacements and deformations are used to quantitatively determine (S4) a value of at least one mechanical parameter, such as the HMI elastic modulus $E_{HMI}$, based on the applied known acoustic force and the measured displacements and deformations.

The processor 30 may include a user interface (UI) 31 to allow the entry of commands and the display or other output of data including calculated quantities, graphical outputs showing predicted or measured data such as strain and/or stress maps, anatomical images, etc.

The system 100 can further include a scanning mechanism (not shown but may include a phased array or mechanical scanning system) for moving the focused ultrasound energy 13 to scan its focal point over a region in the sample to be imaged and applying the acoustic force F at different target locations 60, the imaging transducer 11 taking image sequences at corresponding locations. The processor 30 can be further configured to measure at each location the axial displacement of the target location due to the applied acoustic force and to determining the mechanical property, such as elasticity, of the sample at different target locations. Furthermore, the processor 30 can be further configured to generate a map of the measured mechanical property, such as elasticity, of the sample at different target locations to obtain a map of the variations in elasticity of a sample tissue or organ.

In an embodiment, the processor 30 calculates the tissue properties in a scanned zone defined by a specific programmed array of volumes to be forced and imaged. That is, the processor derives the mentioned map of elasticity. In the embodiment, the properties are then compared to threshold levels stored in the system and the scanning is repeated again at higher density in volumes within or adjacent the volumes where the threshold levels (e.g., elasticity) are exceeded. For example, a suspicious subvolume of an organ surveyed may be identified by the properties of one or more scanned volumes, which properties are out of range. The processor 30 may be programmed to scan the subvolumes around the suspicious volume at a higher density, scan the same subvolumes for second set of data samples, or both. In addition, or alternatively, the processor 30 may be programmed to drive the FUS at a higher frequency and map the suspicious tissue area at a higher resolution to narrow down the areas affected by abnormal tissue properties.

Figure 4:
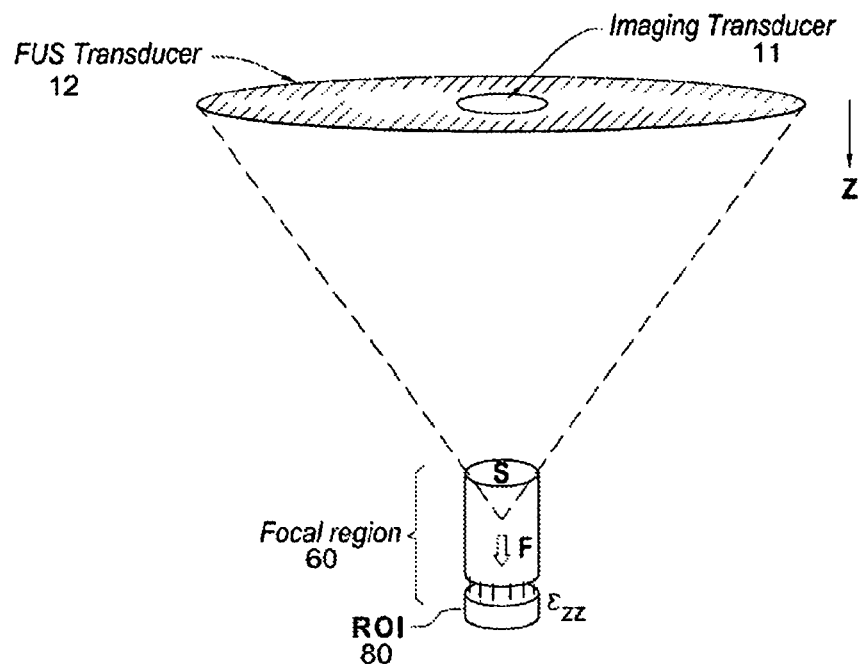
FIG. 4 is a schematic representation of a system generating and applying an acoustic force at a focal region within a sample according to embodiments of the disclosed subject matter.
Figure 5:
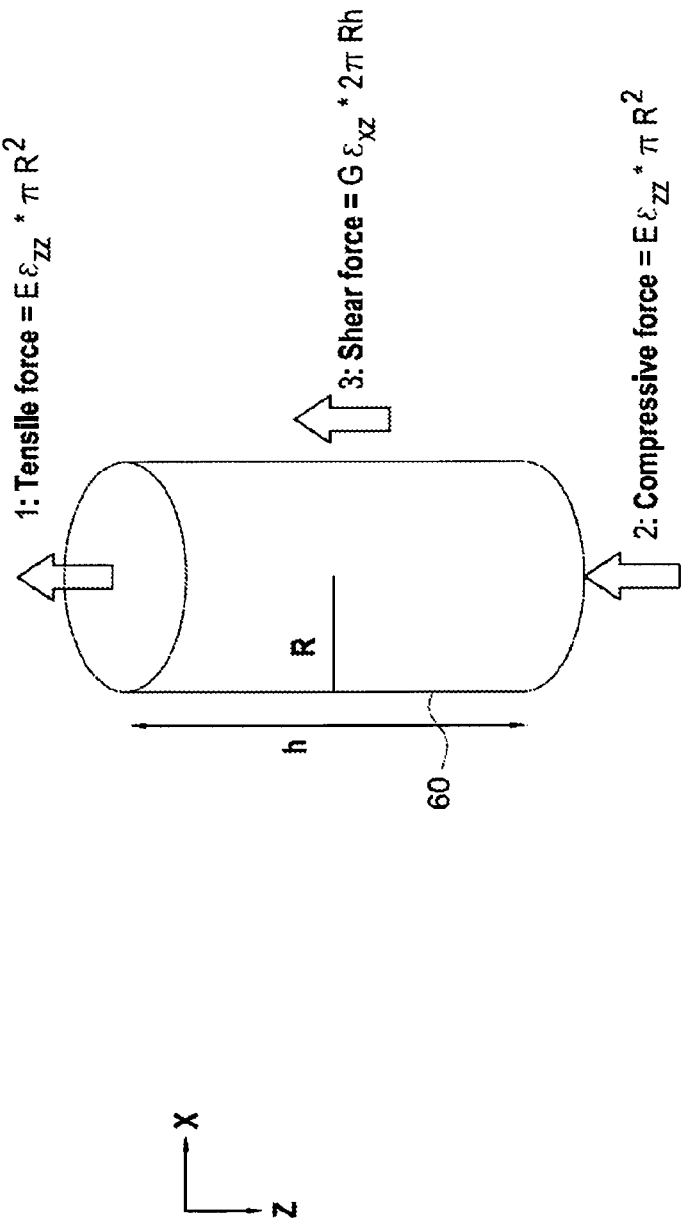
FIG. 5 shows forces acting on a focal region having a cylindrical shape.

The focal region 60 is modeled as a cylindrical region (see FIGS. 3(c), 4 and 5) where the volumic acoustic radiation force F is uniform. The focal region 60 is thus similar to a rigid cylindrical piston that exerts an oscillating internal force to the underlying tissue and may be modeled as such. This is an approximation since the actual radiation force may have a non-cylindrical spatial distribution (see FIGS. 3(a), and 3(b)). The validity of such an approximation has been evaluated. This cylindrical region may be assumed to act as an oscillating rigid piston. As represented in FIGS. 4 and 5, it is proposed to define the 1D HMI elastic modulus $E_{HMI}$ as the ratio between the compressive stress $\sigma_{compression}$ experienced by the tissue exerted by the piston and the axial strain $\epsilon_{zz}$ measured in an infinitesimal volume located below the focal region:

$$E_{HMI}(t) = \frac{\sigma_{Compression}(t)}{\varepsilon_{zz}(t)} \quad (1)$$

where $\sigma_{compression}$ can be expressed as the total force F exerted by the piston over the cross-sectional surface S of the focal region:

$$\sigma_{compression} = \frac{\iiint_{volume} f_v dV}{S} \quad (2)$$

where $f_v$ is the volumic acoustic radiation force within the focal region 60. The experimental setup used is dynamic (hence, $f_v$, is time-dependent). As an approximation, $E_{HMI}$ is defined as the ratio of the maximum $\sigma_{compression}$ divided by the maximum measured strain $\epsilon_{zz}$. $E_{HMI}$ is therefore defined as:

$$E_{HMI} = \frac{\max(\sigma_{Compression})}{\max(\varepsilon_{zz})} \quad (3)$$

This method requires knowledge of the acoustic radiation force. The experimental pressure profile was obtained using a needle hydrophone in water according to published methods. The corresponding 3D acoustic radiation force distribution was used as input in both simulations and experiments described (see FIG. 7A). Acoustic radiation force $f_{exp}$ was calculated as:

$$f_{exp} = \frac{2\alpha I}{c_s} \quad (4)$$

where I is the acoustic intensity, $c_s$ the speed of sound ($c_s$=1530 m/s), and $\alpha$ the acoustic absorption of the medium. Absorption a was measured by transmission on the same polyacrylamide gels as those used in the phantom study. It was found to be equal to $\alpha$=0.25 cm-1 at f=4.5 MHz. This value was chosen for the calculation of the input force for both finite-element and phantom studies.

The volumic force distribution was modeled as a cylindrical region $\Omega$ inside which the volumic force $f_\Omega$ was assumed to be uniform (hence acting as a rigid piston). The size of this region was chosen as the region outside which the volumic force is less than one tenth of the peak volumic force, resulting in a region 3 mm in length by 0.9 mm in diameter. The uniform volumic force $f_\Omega$ was calculated as the average of the actual experimentally measured volumic force $f_{exp}$ within $\Omega$:

$$f_\Omega = \frac{\iiint_\Omega f_{exp} dV}{V_\Omega} \quad (5)$$

where $V_\Omega$ is the volume of the cylindrical region $\Omega$. The volumic force value $f_\Omega$ was used as input volumic force in equation 2 for both simulations and experiments.

Finite-element simulations were performed using the commercial ABAQUS software (Abaqus 6.8, Simulia, Providence, R.I., USA). Three types of simulations were carried out. First, the error resulting from the assumption of a uniform acoustic radiation force within the focal region was evaluated. Second, the correlation between the HMI modulus $E_{HMI}$ and the actual Young's modulus E was estimated in homogeneous numerical phantoms. Finally, the influence of heterogeneity of the medium was evaluated.

For all the studies, axisymmetric models were used, and the geometry of the medium was chosen as cylindrical (50 mm in length*50 mm in diameter). The dynamic problem was solved in an implicit scheme (time step=0.005 s, total duration=1 s). For all the simulations, the excitation frequency was chosen to be f=10 Hz. The focal region 60 was located at the center of the axis of revolution, with dimensions as previously described. A zone of mesh refinement around this focal region was delimited (length=10 mm, radius=2 mm).

As explained above, the proposed method assumes the acoustic radiation force is uniform within a cylindrical region that acts as a rigid indenting piston (FIG. 4). In reality, the distribution of the acoustic radiation force is more complex, although almost all of the energy is concentrated in the focal spot region. Next, the error related to such a choice of modeling is evaluated. A homogeneous numerical phantom was used, where force profiles were implemented, namely, the actual experimental force and the resulting uniform equivalent. The average strain values measured below the focus at the center line were compared. The Young's modulus of the medium was chosen to E=2 kPa.

The Young's modulus E of the numerical phantom was varied (0.5 kPa, 1 kPa, 2 kPa, 5 kPa, 10 kPa, 20 kPa). For each case, the average strain in the center line was measured, allowing the calculation of the HMI modulus $E_{HMI}$. $E_{HMI}$ was compared to the input Young's modulus E in each case. The influence of medium heterogeneity on the measurement of $E_{HMI}$ was evaluated. A spherical inclusion was embedded within the numerical phantom around the focal region. The background stiffness was fixed to $E_{background}$=1 kPa while $E_{inclusion}$=10 kPa. The diameter of the inclusion was varied between 4, 6, 8, 10 and 12 mm. For each case, $E_{HMI}$ was calculated.

The HMI modulus $E_{HMI}$ was measured on six polyacrylamide (PA) phantoms (concentrations of 15%, 20%, 25%, 30%, 35% and 40%), and compared to the Young's modulus E measured by mechanical testing. For each gel, the same liquid mixture (before cross-linking) used for the construction of HMI phantoms was used to make samples for mechanical testing.

For HMI experiments, parallelepiped-shaped phantoms were prepared (approx. 10 cm*5 cm*5 cm). Agar powder was added to each mixture for scattering at a concentration of 4%. The amplitude modulation (AM) frequency was 20 Hz, resulting in an excitation frequency of f=40 Hz. The size of the window for displacement estimation was equal to 1.8 mm, with an overlap of 90%. The compressive strain was calculated as the 1D gradient of the axial displacement by using the least square estimator method using a kernel of 7 pixels.

For mechanical testing, cylindrically-shaped samples were prepared for each gel (N=5-8 per gel, diameter=12 mm, thickness=2.5-3.5 mm) and were tested on an ARES rheometer (TA Instruments, New Castle, Del., USA). Dynamic analysis was performed at frequencies between 1 Hz and 10 Hz at E=0.5% strain. The value of the shear storage modulus $G_{Mech.Test.}$ measured at f=10 Hz was chosen as the reference value, and the Young's modulus was obtained by $E_{Mech.Test.}=3\ G_{Mech.Test.}$ under the assumption of quasi-incompressibility.

Figure 6:
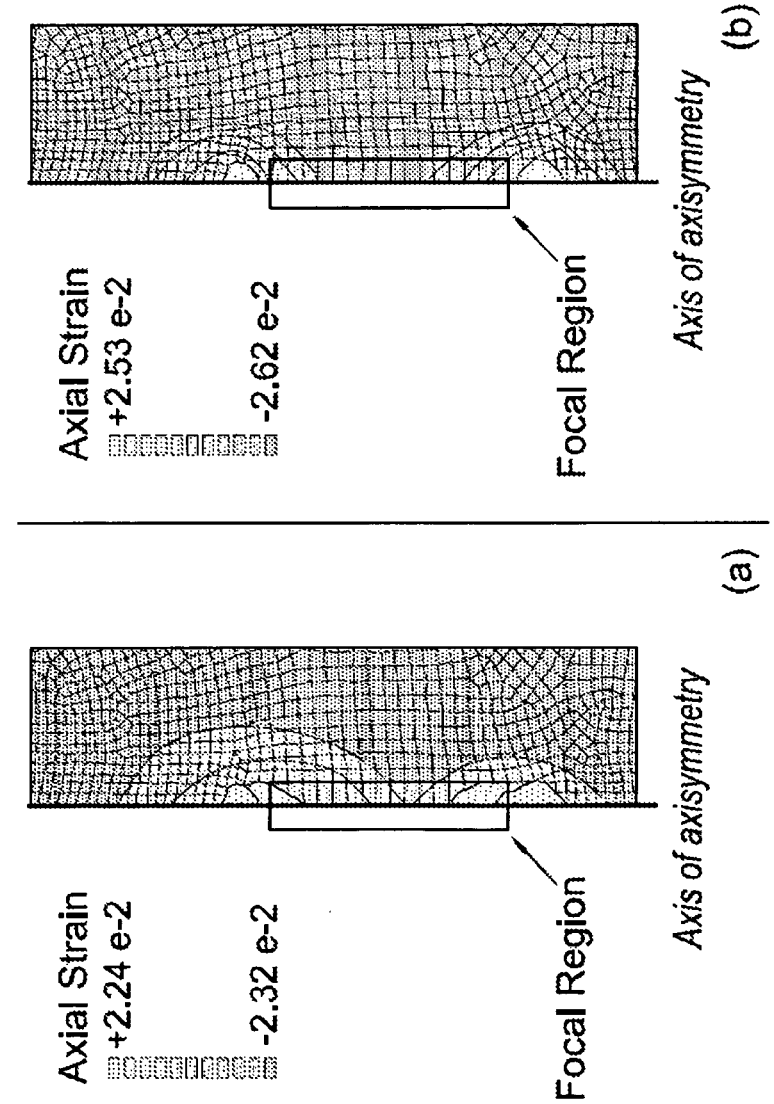
FIGS. 6(a) and (b) show axial strain fields around a focal region for an actual force field and a modeled force field.

Evaluation of the Error Under the Uniform Force Assumption:

The maximum compressive strain values $\epsilon_{zz}$ were compared in two cases, namely, (1) using the actual force field derived from experimental measurements and (2) using the corresponding modeled force field uniform within the focal region. FIG. 6 illustrates the strain profile around the focal region (zoomed) for both cases. It was found that the two strain distributions were very similar. Compressive strain $\epsilon_{zz}$ was averaged within a region of interest (ROI) of approximately 0.5 mm in length and 0.2 mm in diameter. The values of $\epsilon_{zz}$ in the uniform case differs from the $\epsilon_{zz}$ measured using the actual force field, but this difference was deemed to be relatively limited ($\approx$13% relative error).

Figure 8:
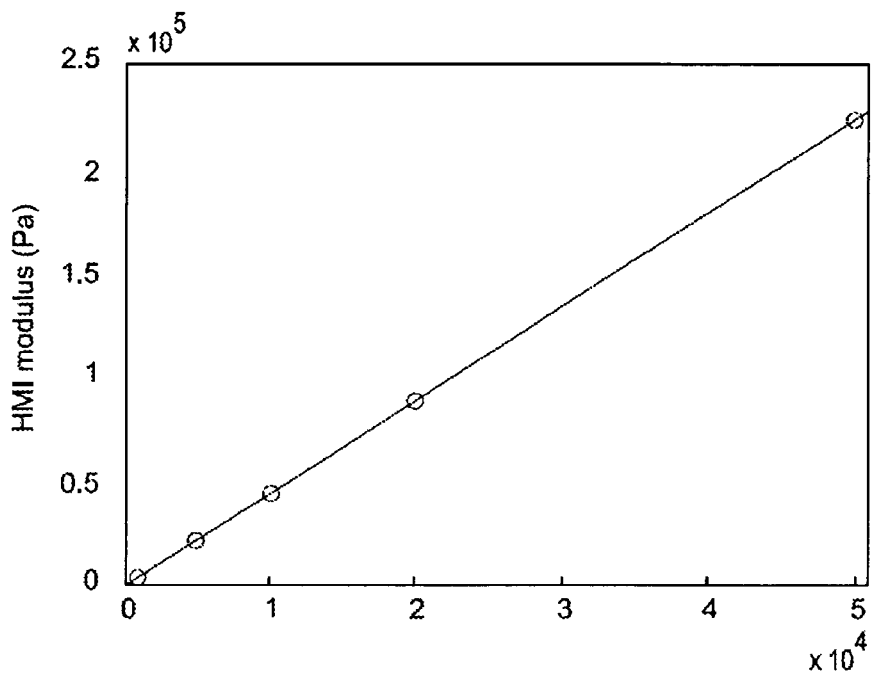
FIG. 8 is a graph of a correlation between measured elastic modulus and Young's modulus.

HMI Modulus $E_{HMI}$ Versus Young's Modulus E:

As in the previous simulation, the maximum compressive strain was measured in all tested cases. It was used to calculate $E_{HMI}$ according to equation (1). Excellent correlation was found between HMI modulus $E_{HMI}$ and the input Young's modulus E. FIG. 8 illustrates $E_{HMI}$ versus E for E varying between 0.5 kPa and 20 kPa.

Figure 10:
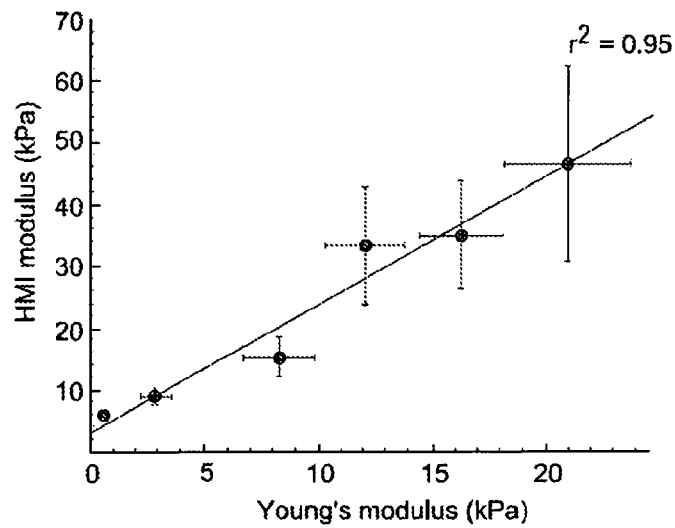
FIG. 10 shows a correlation between measured elastic modulus on a polyacrylamide phantom and Young's modulus.
Figure 9:
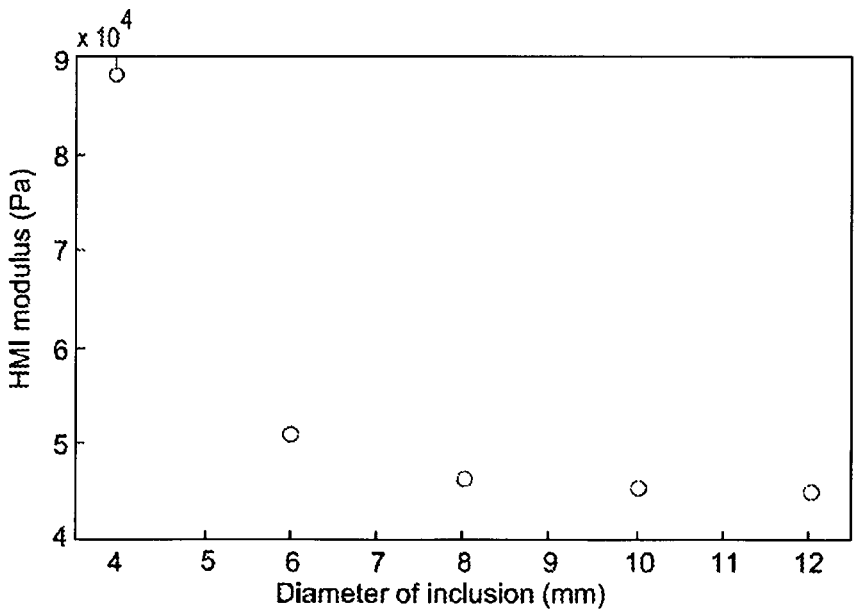
FIG. 9 is a graph of measured elastic modulus vs. diameter of inclusion in the case of a heterogeneous numerical phantom.

Dependence on Heterogeneity:

The inclusion size was varied between 4 mm and 12 mm in diameter (focal region length=4 mm). Results are shown in FIG. 9. For an inclusion size of 6 mm or higher, the HMI modulus $E_{HMI}$ was found to be very similar to the HMI modulus $E_{HMI}$ found in the uniform case (average relative difference=12%). For an inclusion size of 4 mm, the HMI modulus $E_{HMI}$ was found to be significantly different. This shows that $E_{HMI}$ is independent of the inclusion size as long as the inclusion is approximately two times larger than the focal region. Very good correlation ($r^2$=0.95) was found between the Young's modulus E and the HMI modulus $E_{HMI}$. The average ratio between the two moduli was found to be $E_{HMI}/E\approx2.3$. FIG. 10 illustrates the HMI modulus $E_{HMI}$ versus the Young's modulus E for the 6 tested gels. In this study, only the peak strains and stresses were used, and their temporal variation has not been used. Currently, $E_{HMI}$ can be measured over the typical HMI excitation range (f=10 Hz-200 Hz, for example). Ongoing work is carried out on the use of the dynamic information to infer additional information such as viscoelastic properties, as well as their dependence on the excitation frequency.

Thus, this study has shown on both numerical and physical phantoms that the correlation between the HMI elastic modulus $E_{HMI}$ and Young's modulus E is very high. Hence, the HMI modulus $E_{HMI}$ conveys full information on local linear elastic properties.

The numerical study has also established the very high correlation between $E_{HMI}$ and E, and has shown the robustness of $E_{HMI}$ as it is independent on the heterogeneity of the medium. In other words, $E_{HMI}$ can be measured locally point-by-point almost independently of the elasticity distribution around this point, as long as the typical heterogeneity size is larger than the focal region (typically >5 mm at 4.5 MHz). This makes this measurement particularly robust, allowing to map the elasticity of a medium by changing the point of measurement.

Very high correlation was found as well between $E_{HMI}$ and E in the phantom study. The standard deviation of the measurements was significant, especially in the most rigid phantoms (30%, 35% and 40% concentration), where the measured strain values were lower and the signal to noise ratio was poorer than in softer gels. In order to overcome this uncertainty and enhance the accuracy of the method, the input force can be increased so that the SNR increases as well. However, in this phantom study, the same input force was used for all the phantoms in order to allow direct comparison in the same conditions.

It has been shown that the approximation of a cylindrically-shaped focus inside which the volumic force is uniform does not yield significant error compared to the actual force distribution. However, there is an additional source of uncertainty, namely, the value of the acoustic attenuation. For these phantoms, the acoustic attenuation was estimated to $\alpha$=0.045 cm$^{-1}$ MHz$^{-1}$. In practice, the acoustic attenuation varies case by case depending on which tissue is studied. It can be estimated according to the different sources existing in the literature, but this will result most probably in an approximation of its actual value. However, due to the linear relationship between acoustic radiation force and acoustic attenuation (equation 4), an inaccurate estimation of $\alpha$ will affect the absolute values found for $E_{HMI}$, but it will not affect the correlation that exists between $E_{HMI}$ and the intrinsic Young's modulus E. A limitation to this method would be the study of an organ where the acoustic attenuation varies dramatically within the tissue, since in that case, the spatial variation of $E_{HMI}$ not be only related to spatial variation of E, but also to the spatial variation of the attenuation.

Although the proposed devices, systems and methods measure a stiffness parameter $E_{HMI}$ that is strongly correlated with, but not equal to the actual elasticity, they provide the following advantages over shear-wave based methods. For example, shear wave based methods allow the quantitative measurement of the local shear modulus, for example, wave-based HMI. Although shear wave methods may allow the quantitative estimation of viscoelastic properties, they suffer from significant limitations related to shear wave phenomena, such as wave reflections due to heterogeneity, diffraction, and mode conversion. Moreover, they have resolution limitations that are directly related to wavelength limitations. Mitigation of the resolution limitations by increasing the excitation frequency increases attenuation and decreases signal-to-noise ratio. The frequency ranges that can be effectively used in shear wave based methods are also constrained as a result of complex physical and inverse problem-related issues. In contrast, the present devices, methods and systems may be employed to measure the local elasticity at a submillimetric scale in a straightforward manner. Many applications are possible including deep tissue property mapping or the measurement of local elastic properties of small samples or organs. In embodiments, the focal size is selectable based on FUS frequency.

Existing methods may use the acoustic radiation force for estimating mechanical properties of biological tissues. Among these methods, Acoustic Radiation Force Impulse Imaging (ARFI) and traditional HMI consist in measuring the tissue displacement resulting from an internal excitation. The former method focuses particularly on the response in the temporal domain (by measuring tissue relaxation) and the latter one on the response in the frequency domain (by imposing a single frequency excitation). However, the displacement alone is only a qualitative indicator of tissue elasticity, since it is highly sensitive to boundary conditions and heterogeneity of the medium. These methods are therefore particularly useful for certain clinical diagnostic purposes, but they remain limited for biomechanical applications that aim at quantitatively measuring tissue elasticity. Several methods propose to use the shear wave generated internally, such as Shear Wave Elasticity Imaging and shear wave-based HMI. In both cases, the acoustic radiation force is oscillatory, the propagation of the shear wave is imaged by a second transducer and elastic properties are measured from the estimated shear wave velocity. This is the same principle as the one used by Supersonic Shear Imaging (SSI), where multiple foci are excited to produce a quasi-plane shear wave. Although all these methods provide a quantitative estimation of the shear modulus, they are associated with typical limitations of shear wave-based methods as explained previously, especially in terms of resolution and inaccuracy in significantly heterogeneous materials.

Since there is a good correlation between the HMI elastic modulus $E_{HMI}$ and the actual Young's modulus E, the systems and methods may include a further step of calculating the actual Young's modulus E and providing this as a quantitative measurement displayed from a user interface. The conversion can be performed by a processor by means of a look up table, a conversion formula, or other means.

In embodiments, shear and Young's modulus are measured using the geometric approximation described above with reference to FIG. 4 but the strain is mapped in a region surrounding the focal region and the force balance contributions for shear and compression-tension are accounted for respectively. In the present embodiments, the processor 30 may be used to convert the acquired image data sequences to displacement data $u_z$ and to calculate a parameter of a mechanical property of the tissue or organ based on the displacement data $u_z$ and the known acoustic force F. The volumic force F can be measured, for example as part of the transducer calibration, and its spatial profile can be therefore known (see FIG. 7A). For the mechanical property of elasticity, the parameter to be determined may be the elastic modulus of the tissue or organ. Since the force balance equation of the focal region 60 relates to both the axial and shear strains exerted upon the focal region 60 by the force F, the elastic modulus and the applied force F (see FIG. 5), the elastic modulus can be quantitatively determined from the measured axial and shear strains based on the known (predicted) applied force F. The local elastic properties of the tissue or organ can be then estimated based on the determined elastic modulus.

The axial ($d_{uz}/d_z$) and shear deformations ($d_{ux}/d_z$) that result from the applied force F can be obtained by calculating the spatial derivatives of the measured axial displacements $u_z$. The elastic modulus may be represented as the stress imposed by the "piston" on the underlying tissue divided by the measured uniaxial strain. It is a stiffness index, which is equal to the ratio between the applied stress and the resulting uniaxial strain. The elastic modulus can be calculated from the axial and shear strain values measured around the focal region 60.

Figures 11A, 11B:
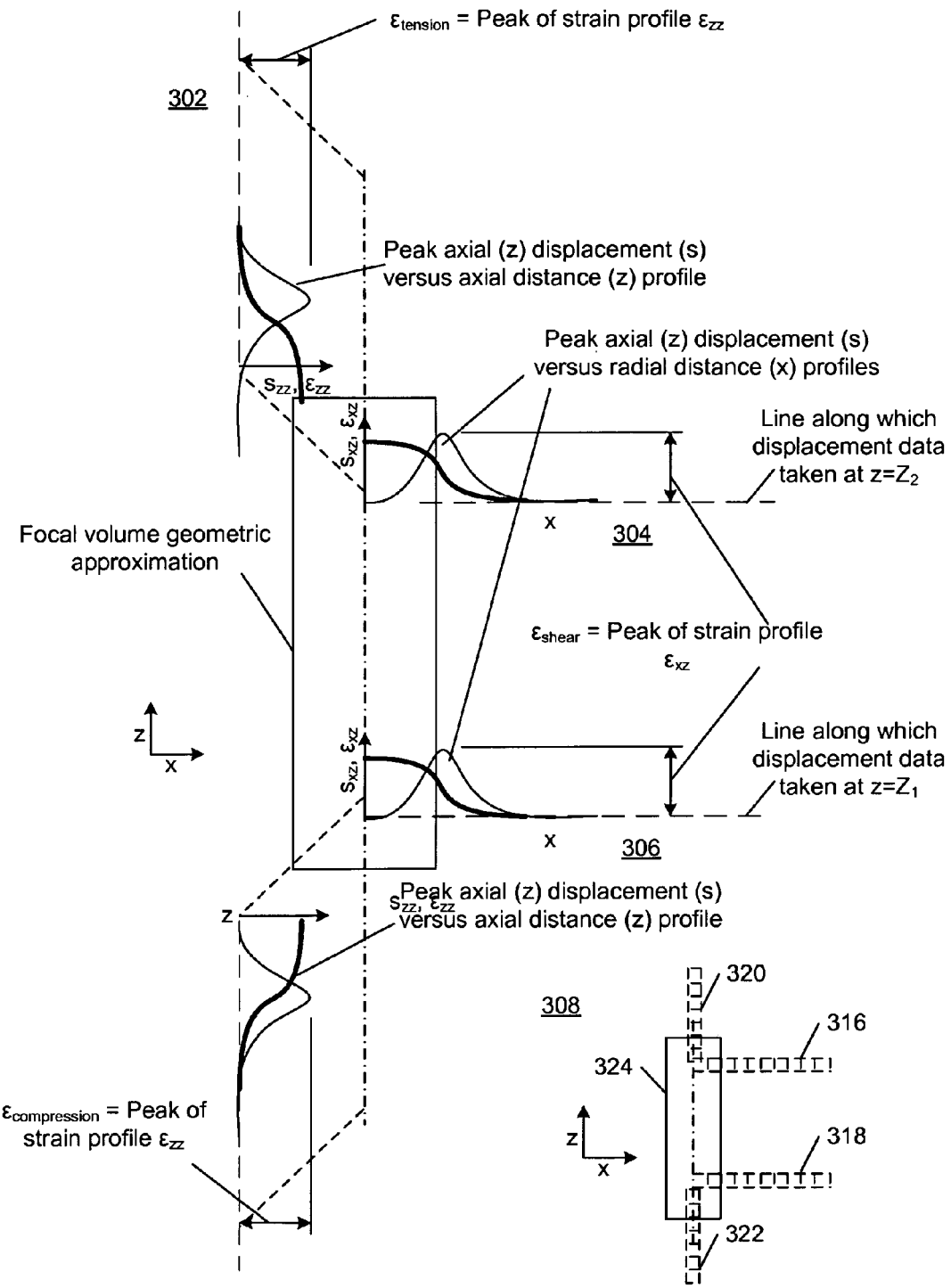
FIGS. 11A and 11B illustrate data collection and/or analysis according to a sparse strain field for calculating an elastic property of a portion of a tissue volume.

FIGS. 11A and 11B illustrate data collection and/or analysis according to a sparse strain field for calculating an elastic property of a portion of a tissue volume. In embodiments, a map of displacements may be derived from the RF data to generate a two or three dimensional strain field map. The peak values near the boundaries of the geometric approximation, for example, a cylinder, can be selected from the map for use in balancing the force equation and thereby derive the elastic modulus from which Young's modulus may be derived. Note the elastic modulus $E_{HMI}$ may be used directly, for example to identify tissue property inhomogeneity that might reveal pathology, according to any of the disclosed embodiments. FIG. 11A shows sample lines along which a two dimensional strain field map may be taken in order to select the peak strains. Equivalently, FIG. 11A may be considered to show measurement lines along which RF displacement data is derived to generate the peak strain values that are used to balance the force equation. At 302, the peak displacement amplitude versus axial distance at the centerline of a (cylinder) focal region is shown. The strain profile is also shown over the same line. FIG. 11B shows an example of portions of a strain map that may be generated and analyzed for the peak shear, compression, and tensile components that are used to balance the FUS volumic force. Instead of two radial sweeps 316 and 318, only one or several more may be generated. Or, as mentioned, a map of the entire surrounding volume may be generated. Other variations are possible, for example, the zone in which the FUS force acts can be made of multiple parts and/or the approximation may accommodate variation of the force over the focal volume and tension, shear, and compression regions acting between them. The focal volume may be modeled as geometric approximations that are shapes other than cylinders.

The disclosed subject matter therefore include device, method, and system embodiments for using the acoustic radiation force resulting from focused ultrasound energy in order to generate an internal force remotely (which can be represented as an "internal" piston) and to measure quantitatively tissue elasticity in vivo and non-invasively. For this purpose, two ultrasound transducers may be employed. A first of the two may include a Focused Ultrasound (FUS) transducer, and a second of the two may include an imaging transducer. The FUS may generate an ultrasound wave at a predetermined frequency (for example at 4.5 MHz) and may be amplitude modulated to generate an acoustic radiation force, oscillating at twice the modulation frequency, at its focus region. The imaging transducer may be confocal and concentric with the FUS transducer. The imaging transducer may be configured to receive the energy from a region around the focus region. Image data is captured at a frame rate, for example, in the range of 100-200 Hz. A processor may be used to convert acquired sequences of image data to displacement data and to derive associated tissue properties. Tissue properties may include Young's modulus. Embodiments of the disclosed subject matter include systems configured to implement the methods described as well as devices for implementing the methods.

In further embodiments, the resolution of the measurement can be about the lateral size of the focal region (1 mm diameter) and the excitation frequency can be swept within the f=10 Hz-1000 Hz range. This way the dynamic Young's modulus E can be measured similarly to what is done in dynamic mechanical testing. The magnitude of the excitation can also be changed, in order to study the non linear response of the tissue. In some exemplary embodiments the acoustic intensities can be limited to those that do not alter tissue structural integrity (e.g., W<500 W/cm$^2$ approximately).

Further, in some embodiments, the disclosed methods and devices can be used at high acoustic intensity to ablate tissue, such as tumor tissue, as well as to monitor the displacements during the ablation process.

In addition to in vitro testing embodiments, in vivo applications of the disclosed subject matter include, for example, measuring the elastic properties of internal organs, including deep organs such as liver or pancreas, for both preclinical (e.g., animal subjects) and clinical applications. The methods can also be used to map the elasticity of such organs (e.g., variation of elasticity within the organ), and to provide an additional raster scanning protocol. The methods can also detect regions that are abnormally stiff (because of the presence of a tumor, for example). In orthopedic tissue applications, the disclosed subject matter can assess, non-invasively, local structural alterations of cartilage tissue resulting from a disease (e.g., a non-invasive measurement of cartilage elasticity). In preclinical applications on, e.g., small animals, the disclosed subject matter can be utilized as a non-invasive, simple method for the follow-up of therapeutic treatments. For example, pancreatic cancer is known to be associated with a dramatic increase in elasticity. Thus, the efficiency of the treatment of such diseases can be monitored by measuring the evolution of the mechanical properties with time in the same subject.

In embodiments, first and second ultrasound transducers are employed to determine, in vivo, the elasticity of a living tissue volume. The first ultrasound (FUS) transducer is a focused ultrasound transducer and the second is an imaging transducer. The FUS transducer may be configured to deliver an amplitude-modulated focused energy beam to a vibrated portion (the "focal volume" in embodiments) of the tissue volume to induce motion in the vibrated portion. The vibrated portion is vibrated over at least one cycle and, in embodiments, multiple cycles. Simultaneously, the imaging transducer acquires RF data from the vibrated portion as well as an adjacent and surrounding portion of the living tissue volume. A processor derives, from the RF data, the peak compression, tensile, and shear strain in the tissue volume adjacent the vibrated portion during one or more cycles of the vibrated portion. The processor may also look up (in a memory), or calculate, the total volumic force applied to the vibrated portion responsive to the frequency, configuration (including the predicted energy distribution), and power of the FUS transducer and predicted tissue properties. In embodiments, the total volumic force is taken as applied over a fixed geometric approximation of the vibrated portion which geometric approximation is taken to vibrate rigidly such that the stress caused by the peak compression, tensile, and shear strains are balanced by the force taken to act on the geometric approximation. In embodiments, the geometric approximation is symmetric such that the RF data may be acquired for only a side of the vibrated portion and an adjacent volume on a side. In embodiments, the shear modulus is taken to be related to an elastic modulus such that the elastic modulus can be derived from an equation that balances the stresses and force acting on the geometric approximation. The processor may calculate the elastic modulus for multiple vibrated portions throughout the living tissue volume to create a map of this property through the living tissue volume. The processor may convert the elastic modulus to a standard modulus such as Young's modulus and store a volume map of this property for the living tissue volume in a memory or non-volatile data store.

Thus, according to embodiments, RF data is acquired in a volume at least on a side, for example, a section as illustrated in FIG. 6 may be acquired and provided in the RF as series of images and cross-correlation between frames used to generate displacement data from which the strains can be determined.

In embodiments, Young's modulus is calculated and quantified by a processor and output on a user interface connected thereto. In embodiments, the system and method are employed in a non-invasive way, for example using a combined FUS and imaging transducer. The combined transducer may be held to an external surface of the body or adjacent the interior of a natural body lumen or inserted in a surgically-created opening. The system permits the determination of tissue properties at deep locations and is not limited to surface tissue.

In embodiments, the excitation frequency is swept by the processor over multiple frequencies, for example, a continuous or piecewise continuous range, for example, in the interval f=10 Hz-1000 Hz, to determine a dynamic modulus such as the dynamic Young's modulus E(f). The magnitude of the excitation can also be changed, to study non linear response of the tissue.

In embodiments, the acoustic intensities are limited such that the intensity does not cause damage. In embodiments, the intensity is limited to avoid alteration of tissue structural integrity. In embodiments, the FUS transducer power is limited to less than about 500 W/cm$^2$.

In embodiments, in brief, the Young's modulus E is calculated from the axial and shear strain values measured around the focal region. The force balance equation of the focal region relates both axial and shear strains, the Young's modulus and the applied force. By measuring the former quantities and by knowing the latter one, the Young's modulus can be estimated. Referring to FIG. 12, the corresponding method embodiments begin with determining an acoustic radiation force S102, which may be measured experimentally using a measurement of acoustic intensity and a measured acoustic absorption of a target medium. The controller 30 may automatically determine acoustic intensity based on a selected frequency. Tables correlating values for acoustic absorption with tissue types and the selected FUS frequency may be stored in a controller 30 and selected via the user interface 31. The imaging device, for example an ultrasound imaging device, then provides displacement profiles S104 from which peak strain are then derived by the controller S106. Then assuming a relationship between Young's modulus and the shear modulus, the FUS total volume force and peak strain values are used to calculate the Young's modulus as discussed with reference to FIGS. 11A and 11B.

Referring to FIG. 13A, the Young's modulus may be measured in a tissue volume (Region A in FIG. 13B) with presumed homogenous properties and then the focal volume moved to a position near a boundary dividing region A from a region B, which may be presumed to have a different Young's modulus (as shown in FIG. 13C). The contribution of forces is be calculated from the corresponding displacement of tissue at the boundary. Here the force (focal volumic force) compensated by the stress on the side and the axial face opposite the boundary is balanced by the pressure-tension force at the boundary permitting the modulus of the material in region B at the boundary to be measured as if an indenter were inserted at the boundary. The boundary may be, for example, the surface of an organ.

Note that in the disclosed embodiments, the focal region was assumed to be a single size. In embodiments, a device and system may be configured to generate focal regions of multiple sizes and shapes. In such embodiments, a first region shape, for example a long thin cylinder is generated and used to provide a first force balance equation with two unknowns, namely a shear modulus and a tension-compression modulus. A second region shape, for example a short stout cylinder is generated and used to provide a second force balance equation with the same two unknowns which may then be solved for. Thus, the focal region shapes so that the relative contributions of the shear modulus and Young's modulus are substantially different, permitting the two modulus values to be backed out of the simultaneous force balance equations.

In all of the embodiments, calculated values may be displayed by user interface 31 or used to trigger reports or other outputs. User interface 31 may include a display, a record generator configured to generate reports which are stored remotely or locally in a memory of the processor 30.

According to embodiments, the disclosed subject matter includes a method for measuring elasticity within a tissue volume. The method includes emitting ultrasound radiation force from a contact region of a surface of a tissue volume energy to vibrate focal region remote from the surface. The method also includes generating image data representing at least a portion of the focal region and a region surrounding the focal region. From image data resulting from the imaging, displacement magnitude data is extracted which characterizes the vibration of the focal region. A net force is determined which causes the focal region vibration. Then, the method calculates an elastic property of the tissue volume within the immediate vicinity of the focal region from the net force and the displacement data. The calculating may depend on a relationship between strain and the elastic property. The calculating may include calculating an elastic property responsively to displacement data representing a magnitude of deformation of portions of the tissue volume at multiple locations on the boundaries of the focal region. The extracting may include determining displacements at multiple locations along lines running toward and away from the focal region. The focal region may be an approximately cylindrical volume, and the calculating may account separately for shear and compression deformation of the tissue volume.

The generating the image data may be performed at the same time as the emitting such that motion is directly caused by the radiation force. The ultrasound radiation force may be generated by modulating a transducer power output at a frequency in a range of 10-500 Hz. The emitting and generating may employ ultrasound transducers positioned at a same point of the surface. The calculating may include converting an elasticity magnitude to an estimate of Young's modulus using a lookup table or a curvilinear function. The method may further include automatically repositioning the focal region and repeating the emitting and generating to acquire data representing properties at multiple locations throughout the tissue volume. The elastic property may be an estimate of Young's modulus. The displacements may be substantially in a direction toward and away from the contact region.

According to embodiments, the disclosed subject matter includes a method for measuring elasticity within a tissue volume. The method includes emitting ultrasound radiation force from a contact region of a surface of a tissue volume energy to vibrate focal region remote from the surface. Displacement data is generated which represent at least a portion of the focal region and a region surrounding the focal region. The method includes extracting from a data store, volumic force data representing a net force causing the focal region vibration. The method includes calculating an elastic property of the tissue volume within the immediate vicinity of the focal region from the volumic force data and the displacement data. The calculating may depend on a relationship between strain and the elastic property. The calculating may include calculating an elastic property responsively to displacement data representing a magnitude of deformation of portions of the tissue volume at multiple locations on the boundaries of the focal region. The extracting may include determining displacements at multiple locations along lines running toward and away from the focal region. The focal region may be an approximately cylindrical volume, and the calculating may account separately for shear and compression deformation of the tissue volume. The generating the image data may be performed at the same time as the emitting such that motion is directly caused by the radiation force.

The foregoing methods may include positioning the focal region adjacent to a tissue boundary in the tissue volume and repeating the emitting, generating, and extracting and further calculating an elastic property of the tissue volume on a side of the boundary within the immediate vicinity of the focal region from the volumic force data and the displacement data and an elastic modulus calculated in a previous iteration remote from the boundary.

In any of the methods, the displacement may be toward and away from the contact region.

According to embodiments, the disclosed subject matter includes a method for measuring elasticity within a tissue volume. The method includes vibrating, with ultrasound, a focal region in the tissue volume by directing ultrasound energy in an axial direction and mapping strain magnitudes in the tissue volume in the immediate vicinity of the focal region to generate a strain map. The method further includes extracting from a data store, volumic force data representing a net force causing the focal region vibration and calculating an elastic property of the tissue volume within the immediate vicinity of the focal region from the volumic force data and the strain map.

The strain map may include shear strain data representing first local displacement in the axial direction and compression strain data representing second local displacement in the axial direction. The first local displacement may correspond to a peak shear strain at a first location in relation to the focal region and the second local displacement corresponds to a peak compression-tension strain at a second location in relation to the focal region. The focal region may be approximately cylindrical.

According to embodiments, the disclosed subject matter includes a method for measuring elasticity within a tissue volume. The method includes vibrating, with ultrasound, a first focal region in the tissue volume by directing ultrasound energy in an axial direction, wherein the first focal region has a first axial dimension and a first transverse dimension parallel to and orthogonal to the axial direction and detecting first displacement magnitudes at and within a vicinity of the first focal region. The method further includes vibrating, with ultrasound, a second focal region in the tissue volume by directing ultrasound energy in the axial direction, where the second focal region has a second axial dimension and a second transverse dimension parallel to and orthogonal to the axial direction. The method further includes detecting second displacement magnitudes at and within a vicinity of the second focal region, wherein a ratio of the first axial and transverse dimensions is substantially different from a ratio of the second axial and transverse dimensions. Finally, the method includes calculating approximations of the shear modulus and a Young's modulus from the first and second displacement magnitudes. The calculating may include determining a total force of the focal region. The calculating may include determining total forces exerted by the first and second focal regions. The calculating may include calculating a peak strain rate for each of the first and second displacement magnitudes.

According to embodiments, the disclosed subject matter includes a system with a first ultrasound transducer configured to generate an ultrasound radiation force, a second ultrasound transducer configured for generating ultrasound images, and a digital processor with a user interface, the processor being programmed to execute at least the steps of calculating according to any of the foregoing methods.

It is therefore, apparent that there is provided, in accordance with the present disclosure, a device, method, and system for using the acoustic radiation force resulting from focused ultrasound energy in order to generate an internal force remotely and to measure quantitatively a mechanical property, such as tissue elasticity, in vivo and non-invasively. Many alternatives, modifications, and variations are enabled by the present disclosure. Features of the disclosed embodiments can be combined, rearranged, omitted, etc. within the scope of the disclosed subject matter to produce additional embodiments.

Furthermore, certain features of the disclosed embodiments may sometimes be used to advantage without a corresponding use of other features. Accordingly, Applicant intends to embrace all such alternatives, modifications, equivalents, and variations that are within the spirit and scope of the present disclosure.

What is claimed is:

1. A system for determining a mechanical property of a biological sample, the system comprising:
    an acoustic force generating device to remotely apply an acoustic force to a target location within the sample volume to induce sample displacement along an axial direction at the target location, wherein the axial direction is the direction of the applied acoustic force, the acoustic force generating device including an amplitude-modulated focused ultrasound transducer that focuses ultrasound energy at the target location to oscillate a focal region at the target location at approximately twice a modulation frequency responsively to an acoustic radiation force generated by the focused ultrasound transducer;
    a displacement measuring device configured to, simultaneously with a force generated by the force generating device, acquire acoustic data representing an induced sample displacement along the axial direction from the target location;
    the displacement measuring device being configured to measure a displacement of the sample at the target location and at least another location along the axial direction so as to permit a determination of an axial strain of the sample;
    a processing device configured to determine an axial displacement of the target location along the axial direction from the acquired acoustic data and to calculate the axial strain therefrom, the processing device being further configured to determine a deformation of the target location along a direction orthogonal to the axial direction by calculating a spatial derivative of the measured axial displacement, the processing device being further configured to determine a mechanical property of the sample based on the applied acoustic force and the axial displacement;
    the processing device being further configured to generate an estimate of modulus of elasticity of the sample from the axial strain, and the deformation along a direction orthogonal to the axial direction.

2. The system of claim 1, wherein the focal region is a substantially cylindrical region in which the acoustic radiation force is approximately uniform.

3. The system of claim 1, wherein the focused ultrasound transducer is modulated using a signal having a frequency between 5-500 Hz.

4. The system of claim 1, wherein the measuring device includes an ultrasound imaging transducer for receiving ultrasound image data from the target location simultaneously with the application of the acoustic force.

5. The system of claim 4, wherein the ultrasound imaging transducer includes a pulse-echo transducer operating at a frequency of about 7.5 MHz to acquire sequences of ultrasound image data at a frame rate of 100-200 Hz.

6. The system of claim 4, wherein the ultrasound imaging transducer includes a phased array operating at a frequency of about 3.3 MHz to acquire sequences of ultrasound image data at a frame rate of 200-400 Hz.

7. The system of claim 4, wherein the acoustic force generating device is shaped so as to surround the ultrasound imaging transducer.

8. The system of claim 7, wherein the acoustic force generating device is confocal and concentric with the ultrasound imaging transducer.

9. The system of claim 4, wherein the processing device is configured to convert the ultrasound image data to axial displacement data using a cross-correlation technique.

10. The system of claim 9, wherein the processing device is configured to derive a quantitative value of a parameter of the mechanical property of the sample based on the applied acoustic force and the axial displacement data.

11. The system of claim 10, wherein the mechanical property is elasticity and the parameter is an elastic modulus.

12. The system of claim 11, wherein the elastic modulus is a harmonic motion imaging elastic modulus.

13. The system of claim 12, wherein the harmonic motion imaging elastic modulus is derived based on calculated spatial derivatives of the axial displacement.

14. The system of claim 1, wherein the magnitude of the acoustic force is previously determined based on a relationship between the acoustic force, the acoustic intensity of the acoustic force generating device, the speed of sound, and the acoustic absorption of the sample.

15. The system of claim 14, wherein the acoustic intensity is less than 500 W/cm$^2$.

16. The system of claim 1, further comprising a scanning mechanism for moving the focused ultrasound energy to scan its focal point over a region in the sample to be imaged and applying the acoustic force at different target locations, the measuring device acquiring acoustic data relating to induced sample displacement from each corresponding target location, wherein the processing device determines the mechanical property of the sample based on the axial displacement determined at the different target locations.

17. The system of claim 16, wherein the processing device is further configured to generate a map of the measured mechanical property of the sample at different target locations.

18. The system of claim 17, wherein the processing device is configured to generate a map of the elasticity of the sample.

19. The system of claim 1, wherein the sample is one of a biological tissue and an internal organ of a subject, the system being located outside the subject.

20. The system of claim 1, used for remote in vivo measurement of elastic properties of internal tissues and organs located within a subject.

21. A method for determining a mechanical property of a sample, comprising:
applying remotely an acoustic force to a target location within the sample to oscillate a focal region at the target location at approximately twice a modulation frequency responsively to the acoustic force, the oscillating focal region exerting an acoustic force on a predetermined region of the target location which surrounds the focal region to thereby induce sample displacement at the target location along an axial direction, wherein the axial direction is the direction of the applied acoustic force;
simultaneously measuring an axial displacement of the target location along the axial direction caused by the acoustic force; and
calculating a quantitative value of a parameter of the mechanical property based on the applied acoustic force, the measured axial displacement, and a deformation of the target location along a direction orthogonal to the axial direction, the deformation being determined from a spatial derivative of the measured axial displacement.

22. The method of claim 21, wherein the sample is one of a biological tissue and an internal organ of a subject.

23. The method of claim 21, wherein the mechanical property is elasticity and the parameter is an elastic modulus.

24. The method of claim 23, wherein the focal region is a substantially cylindrical region in which the acoustic radiation force is uniform.

25. The method of claim 23, wherein the measuring includes acquiring sequences of ultrasound image data from the target location and estimating the axial displacement of the target location from the acquired image data using a cross-correlation technique.

26. The method of claim 25, wherein the acquiring of the image data is at a frame rate of 100-200 Hz by an ultrasound imaging transducer operating at a frequency of about 7.5 MHz.

27. The method of claim 26, wherein the ultrasound imaging transducer includes a phased array operating at a frequency of about 3.3 MHz which acquires sequences of ultrasound image data at a frame rate of 200-400 Hz.

28. The method of claim 21, wherein the acoustic force is generated using an amplitude-modulated focused ultrasound transducer shaped such that it is confocal and concentric with an ultrasound imaging transducer used to measure the axial displacement of the target location.

29. The method of claim 21, wherein the calculating includes calculating a value of the parameter based on a relationship between the parameter, the applied acoustic force, and the axial displacement.

30. The method of claim 29, wherein the acoustic force is previously determined based on a relationship between the acoustic force, the acoustic intensity of an acoustic force generating device used to generate the acoustic force, the speed of sound, and the acoustic absorption of the sample.

31. The method of claim 30, wherein the calculating further includes calculating spatial derivatives of the axial displacement.

32. The method of claim 21, further comprising scanning the sample to determine the mechanical property of the sample at a plurality of target locations.

33. The method of claim 32, further including a raster scanning protocol to generate an elasticity map of the sample.

* * * * *